United States Patent [19]
Levin

[11] Patent Number: 5,860,936
[45] Date of Patent: Jan. 19, 1999

[54] METHOD AND APPARATUS FOR MEASUREMENT, ANALYSIS, CHARACTERIZATION, EMULATION, AND TRANSLATION OF PERCEPTION

[76] Inventor: David N. Levin, 1720 N. LaSalle Dr., Unit 25, Chicago, Ill. 60614

[21] Appl. No.: 691,615

[22] Filed: Aug. 2, 1996

[51] Int. Cl.$^6$ .................................................. A61B 13/00
[52] U.S. Cl. .......................... 600/558; 600/557; 600/559
[58] Field of Search ..................................... 600/558, 557, 600/559

[56] References Cited

U.S. PATENT DOCUMENTS

| | | | |
|---|---|---|---|
| 3,901,215 | 8/1975 | John ......................................... | 600/558 |
| 4,528,989 | 7/1985 | Weinblatt ................................. | 600/558 |
| 4,676,611 | 6/1987 | Nelson et al. ........................... | 600/558 |
| 4,894,777 | 1/1990 | Negishi et al. .......................... | 600/558 |
| 5,461,435 | 10/1995 | Rootzen et al. ........................ | 351/226 |
| 5,482,052 | 1/1996 | Lerner ..................................... | 600/547 |

*Primary Examiner*—Max Hindenburg
*Assistant Examiner*—Pamela L. Wingood
*Attorney, Agent, or Firm*—Welsh & Katz, Ltd.

[57] ABSTRACT

A method is used for measuring perception of an observer using a stimulus output device for presenting stimuli to the observer, and a stimulus manipulation device permitting the observer to modify the presented stimuli by selecting related stimuli from a database of stimuli. The method includes the steps of: a) selecting a sequence of stimuli from the database of stimuli, the stimuli represented as stimulus points contained in a stimulus space; b) determining a reference transformation of a beginning stimulus point of the sequence of stimuli, the reference transformation being presented to the observer by the stimulus output device; c) selecting a limited portion of the sequence of stimuli, the limited portion of the sequence defined between the beginning stimulus point and an ending stimulus point, the limited portion of the sequence being presented to the observer by the stimulus output device; d) determining an observer-defined transformation applied to the ending stimulus point of the limited portion of the sequence such that the observer perceives the observer-defined transformation applied to the ending stimulus point to be perceptually equivalent to the reference transformation applied to the beginning stimulus point; e) selecting a new limited portion of the sequence of stimuli, the new limited portion of the sequence defined by stimulus points selected from the database, at least a portion of the new limited portion having stimulus points different from the stimulus points defining the previously selected limited portion of the sequence; f) determining another observer-defined transformation applied to an ending stimulus point of the new limited portion of the sequence such that the observer perceives the observer-defined transformation to be equivalent to the previous observer-defined transformation; and g) performing steps (e) through (f) until a predetermined number of limited portions of the sequence of stimuli are processed such that the observer perceives each observer-defined transformation to be equivalent to previous observer-defined transformations.

53 Claims, 13 Drawing Sheets

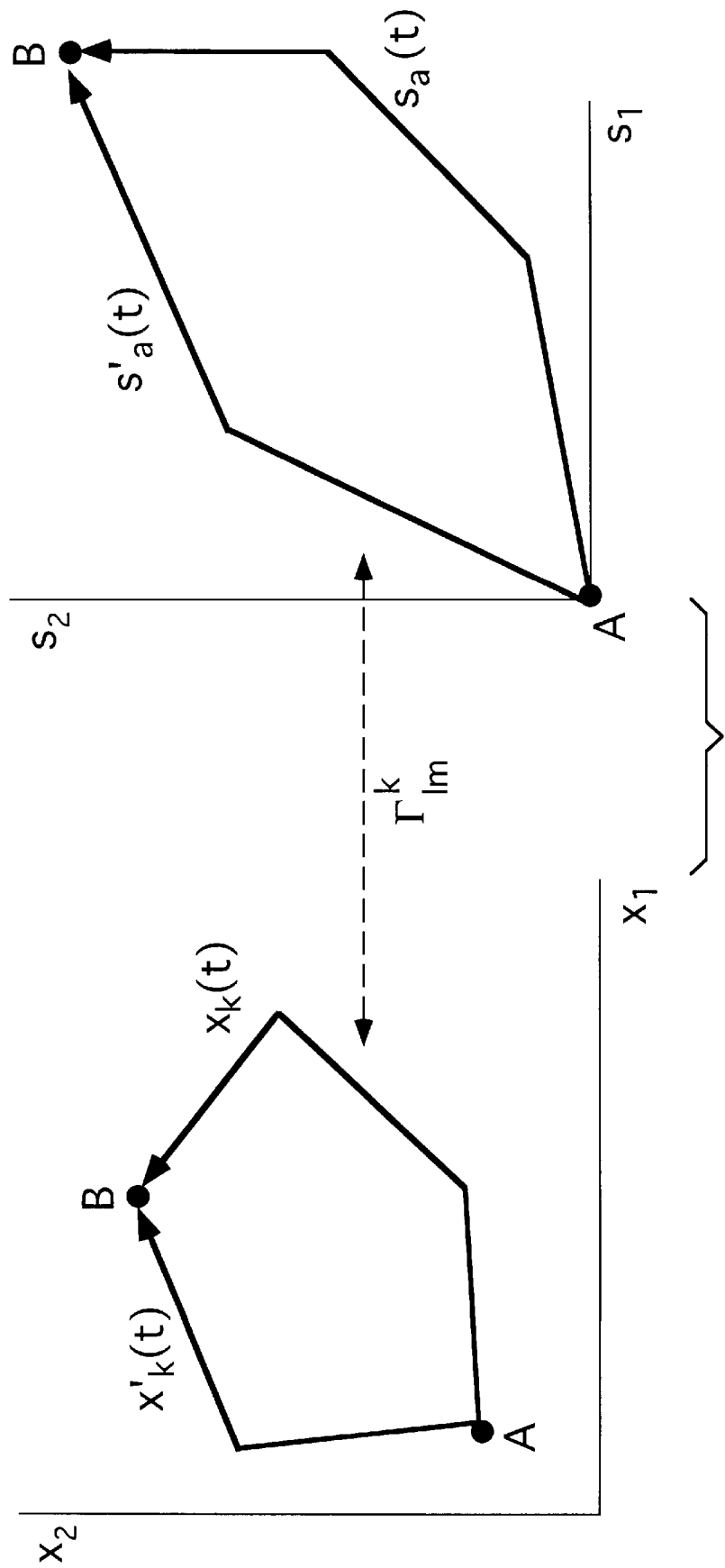

METHOD AND APPARATUS FOR MEASUREMENT, ANALYSIS, CHARACTERIZATION, EMULATION, AND TRANSLATION OF PERCEPTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever

BACKGROUND OF THE INVENTION

I. A dynamically evolving stimulus is often perceived as a series of transformations of another stimulus. For example, an observer may describe the changing appearance of a face in terms of a series of facial expressions: "T closed her left eye halfway, and then she opened it again; after that, she closed her right eye halfway and then closed her left eye halfway again". Classical Western music is based on an explicit set of such transformations. For instance, a listener may describe the evolution of two simultaneously played tones in terms of pitch transformations: "The pitch of the lower note increased by a 'third' and then decreased to its original value; then the pitch of the higher note increased by a third', followed by a similar increase in pitch of the lower note". Static stimuli may be similarly described in terms of imagined transformations of imagined stimuli; e.g. "T had both eyes closed halfway", or "Today, the color is more intense and redder than it was yesterday. All of these descriptions depend on the observer's choice of: 1) a "reference" stimulus (e.g. T's face with both eyes open in the first example; "yesterday's color" in the last example); 2) "reference" transformations which are applied to the reference stimulus (e.g. the half closure of each eye in the first example; changes in the intensity and redness of the color in the last example).

The choice of a reference stimulus is a matter of convenience. For example, the observer could have chosen the reference face with both eyes closed and noted that "T had both eyes halfway open"; in the same way, the proverbial glass of water can be described as half full or half empty. The choice of reference transformations is also a matter of convenience. For example, the first observer could have used transformations which are linear combinations of single eye movements; e.g. eye movements could have been described as changes in: a) the average state of closure of the two eyes and b) the difference between the closure states of the two eyes. In any event, once the reference stimulus and transformations have been chosen, the evolving stimulus can be described in terms of the serial application of these "standard" transformations.

In the above descriptions, it is implicit that the observer perceives certain transformations of the evolving stimulus to be equivalent to the reference transformations of the reference stimulus. In the first example, the observer implicitly equated a transformation of the already transformed face (the final partial closure of the left eye) to an earlier transformation of the reference face (the initial partial closure of the left eye). Likewise, in the musical example, the listener equated a transformation of the already transformed pair of notes (the final pitch change of the lower note) to an earlier transformation of the reference pair of notes (the initial pitch change of the lower note). In discrete form, these equivalence relations express the observer's perception that pairs of stimuli are analogous; e.g. facial expression 4 is to facial expression 3 as facial expression 2 is to facial expression 1. The perceived equivalence of transformations establishes the framework which the observer uses to organize his/her perceptions. If the observer did not perceive such equivalencies, new conventions would have to be established to describe the observed transformations of each state of the evolving stimulus. This can be made more explicit by consideration of the following example. Suppose that the stimulus consists of the movements of a dot on a map of Chicago. The observer might report that "the dot was initially located at the John Hancock Building; then, it moved two miles west, then one mile north, and finally two miles east". In this case, the observer chose to describe the evolving stimulus in terms of an initial reference state, consisting of the dot at the John Hancock Building, and in terms of reference transformations consisting of one mile movements in the north/south and east/west directions. The observer implicitly equated directions and lengths of movements at later stages of the journey to those at earlier stages; e.g. both the first and third legs of the journey were identified as two mile movements in the east/west direction. Such equivalent movements would be easy to identify if the map were covered by a Cartesian grid of east/west and north/south lines having spacing considerably less that one mile.

On the other hand, suppose that there were no grid lines and the observer had to rely on the traditional scale bar together with an image of the "four points of the compass", located in one corner of the map. Then, the observer would have to imagine how to translate these across the map in order to define equivalent directions and lengths at each point along the trajectory of the dot. These "local" compasses and scale bars could then be used to describe each leg of the dot's trajectory. If two observers perceived different equivalence relations of this type, their perceptions of the moving dot would differ. For example, if the two observers had different senses of parallelism, they might have different perceptions of local direction at some points on the map; e.g. observer Ob might give the above-mentioned description while observer Ob' might perceive the final dot movement to be "two miles in a direction slightly south of east". Similarly, in the above-mentioned musical example, two listeners might differ in their identification of the pitch change of the lower note after the pitch change of the higher note. For instance, the first listener might give the above-mentioned description while the second listener might perceive that the lower note's pitch was finally raised by less than a third. This would indicate that the pitch change of the higher note had a different influence on each observer's perception of subsequent changes in the pitch of the lower note.

The present inventive method shows how to use the methods of differential geometry to describe an observer's perception of equivalency between transformations of different stimuli. Specifically, the stimuli are taken to define the points of a continuous manifold. Then, transformations of stimuli correspond to line segments on the manifold. Therefore, an observer's perception of equivalence between transformations of different stimuli defines the equivalence between line segments at different points on the manifold. Mathematically, a method of "parallel transporting" line segments across a manifold without changing their perceived direction or length serves to define an affine connection on the manifold. Thus, an affine connection can be used to describe the experience of almost any observer who perceives such equivalence relations. It should be emphasized that the present inventive method and apparatus does not seek to model the perceptual mechanisms of the observer; the proposed formalism merely provides a way of describing the perceptions of the observer, who is treated as a "black box". Therefore, the technique is applicable to a large variety of perceptual systems (humans or machines) and to a wide range of stimulus types (visual, auditory, etc.). It provides a systematic framework for measuring and characterizing perceptual experiences. For example, aspects of the intrinsic consistency of an observer's perceptions can be characterized by the curvature and other tensors that can be constructed from the measured affine connection. Furthermore, the perceptual performances of two observers can be compared systematically by comparing their affine connections.

SUMMARY OF THE INVENTION

An apparatus and a systematic differential geometric method of measuring and characterizing the perceptions of an observer of a continuum of stimuli is presented and described. Since the method is not based on a model of perceptual mechanisms, it can be applied to a wide variety of observers and to many types of visual and auditory stimuli. The observer is asked to identify which small transformation of one stimulus is perceived to be equivalent to a small transformation of a second stimulus, differing from the first stimulus by a third small transformation. The observer's perceptions of a number of such transformations can be used to calculate an affine connection on the stimulus manifold. This quantity encodes how the observer perceives evolving stimuli as sequences of "reference" transformations. The internal consistency of the observer's perceptions can be quantified by the manifold's curvature and certain other tensors derived from the connection. In general, the measurements of the observer's affine connection characterize the perceptions of the observer.

Differences between the affine connections of two observers characterize differences between their perceptions of the same evolving stimuli. Thus, the present method and apparatus can be used to make a quantitative comparison between the perceptions of two individuals, the perceptions of two groups, or the perceptions a specific observer and a group of observers. The same apparatus can use these measurements to generate a description of a stimulus in terms of other stimuli, that would agree with a description generated by the observer of interest. In this sense, the apparatus can emulate the perception of the observer. The affine connections of two observers can also be used to map a series of stimuli perceived by one observer onto another series of stimuli, perceived in the same way by the other observer. Specifically, the apparatus can "translate" or "transduce" sets of stimuli so that one observer describes one set of stimuli in the same way as the other observer describes the "transduced" set of stimuli.

The novel invention differs radically from all other known methods of measuring and characterizing perception (Julesz, Bela. Dialogues on Perception. Cambridge Mass.: MIT Press, 1995). Specifically, most of these other known methods are based on well-defined models of the perceptual mechanisms of the observer. Some of these models attempt to mimic the known or hypothesized physiology of the human visual or auditory tracts (Spillmann, Lothar and Werner, John S. (Eds.). Visual Perception: the Neurophysiological Foundations. New York, N.Y.: Academic Press, 1990). For example, they may attempt to model the action of the retina, the cochlea, the layers of the visual or auditory cortex, or other areas of the nervous system. Other investigators (Marr, David. Vision. New York, N.Y.: W. H. Freeman, 1982) have proposed computational models of visual or auditory processing. These models may take the form of neural networks or signal processing algorithms that are meant to extract specific types of information from specific classes of visual or auditory stimuli. In contrast to all of these other methods, the invention described herein treats the observing system (human or non-human) as a "black box". The novel inventive method utilizes the methods of differential geometry to parameterize the way in which the observer perceives stimuli relative to other stimuli, without making any hypotheses about the mechanisms of perception. The parametrization can then be used to characterize the performance of the observer, to compare the performance of the observer to that of other observers, to emulate the perceptual performance of the observer, and to "transduce" stimuli into other stimuli so that one observer perceives one set of stimuli in the same way that the other observer perceives the "transduced" stimuli.

More specifically, the method is used for measuring the perception of an observer using a stimulus output device for presenting stimuli to the observer, and a stimulus manipulation device permitting the observer to modify the presented stimuli by selecting related stimuli from a database of stimuli. The method includes the steps of: a) selecting a sequence of stimuli from the database of stimuli, the stimuli represented as stimulus points contained in a stimulus space; b) determining a reference transformation of a beginning stimulus point of the sequence of stimuli, the reference transformation being presented to the observer by the stimulus output device; c) selecting a limited portion of the sequence of stimuli, the limited portion of the sequence defined between the beginning stimulus point and an ending stimulus point, the limited portion of the sequence being presented to the observer by the stimulus output device; d) determining an observer-defined transformation applied to the ending stimulus point of the limited portion of the sequence such that the observer perceives the observer-defined transformation applied to the ending stimulus point to be perceptually equivalent to the reference transformation applied to the beginning stimulus point; e) selecting a new limited portion of the sequence of stimuli, the new limited portion of the sequence defined by stimulus points selected from the database, at least a portion of the new limited portion having stimulus points different from the stimulus points defining the previously selected limited portion of the sequence; f) determining another observer-defined transformation applied to an ending stimulus point of the new limited portion of the sequence such that the observer perceives the observer-defined transformation to be equivalent to the previous observer-defined transformation; and g) performing steps (e) through (f) until a predetermined number of limited portions of the sequence of stimuli are processed such that the observer perceives each observer-defined transformation to be equivalent to previous observer-defined transformations.

BRIEF DESCRIPTION OF THE DRAWINGS

FIG. 4. A manifold is flat and has a symmetric affine connection if and only if every loop-like stimulus trajectory (left panel) corresponds to a loop-like coordinate-independent description (right panel). In this case, any two trajectories, $x_k(t)$ and $x_k'(t)$, with the same endpoints (A and B) correspond to two coordinate-independent descriptions, $s_a(t)$ and $s_a'(t)$, that also have common endpoints;

DETAILED DESCRIPTION OF THE INVENTION

II. Theory

A. Affine-Connected Perceptual Spaces

We assume that we are dealing with a continuous two-dimensional manifold of stimuli, with each stimulus state being assigned a value of the coordinate $x_k$ where $k=1, 2$. Any convenient coordinate system can be used to identify the stimulus states; perceptual experience will be described in a manner that is independent of the definition of this coordinate system. Although the manifold has been assumed to be two-dimensional for purposes of illustration and simplicity, it is straight-forward to generalize most of the following results to higher dimensional stimulus manifolds. Accordingly, a stimulus space having any number of dimensions may be used according to the present inventive method.

Figure 1:
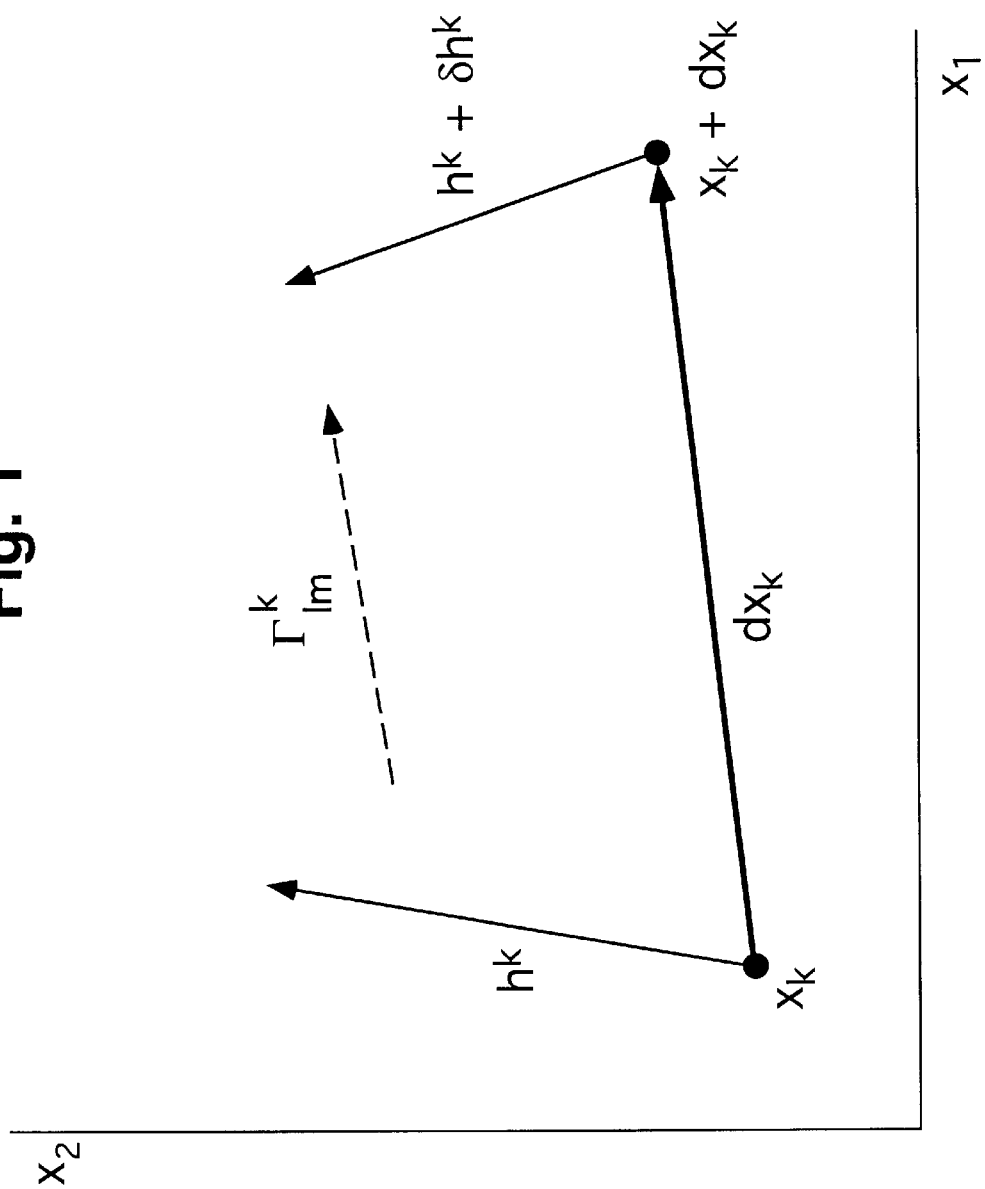
FIG. 1. The observer is assumed to perceive equivalence relations between transformations of stimuli. The vector $h^k$ represents a small transformation of the stimulus state having the coordinates $x_k$. The transformation $h^k + \delta h^k$ of the stimulus at $x_k + dx_k$ is perceived to be equivalent to $h^k$. The affine connection $\Gamma_{lm}{}^k$ relates these perceptually equivalent transformations.

Referring now to FIG. 1, let $h^k$ be a contravariant vector representing the displacement between the infinitesimally close points $x_k$ and $x_k+h^k$; i.e. $h^k$ represents the infinitesimal transformation, which changes the stimulus at $x_k$ into the one at $x_k+h^k$. Let $dx_k$ be the contravariant vector representing the infinitesimal transformation between the stimulus at the point $x_k$ and the one at $x_k+dx_k$. A word about notation: with the exception of $dx_k$, contravariant and covariant quantities are denoted by upper and lower indices, respectively. The following is the fundamental assumption of this novel inventive method: there is a transformation $h^k+\delta h^k$ of the stimulus at $x_k+dx_k$ that is perceived by the observer to be equivalent to the transformation $h^k$ of the stimulus at $x_k$. In geometric language, the observer perceives the transformations $h^k$ and $h^k+\delta h^k$ to have "parallel directions" and equal magnitudes. We expect that $\delta h^k \to 0$ as $h^k \to 0$ since null transformations at the two points should be perceived as equivalent. Furthermore, continuity of perceptual experience dictates that $\delta h^k \to 0$ as $dx_k \to 0$. These two statements imply that $\delta h^k$ is a bilinear function of $h^l$ and $dx_m$ $$\delta h^k = - \sum_{l,m=1,2} \Gamma_{lm}^k(x) h^l dx_m \qquad \text{Eq. (1)}$$

except for terms of order $hdx^2$ and $h^2dx$. This expression is parameterized by the quantity $\Gamma_{lm}^k(x)$, that defines an affine connection on the manifold (Schrodinger, Erwin. Space-Time Structure. Cambridge Mass.: Cambridge University Press, 1963). The value of $\Gamma_{lm}^k$ describes how an arbitrary transformation $h^k$ at $x_k$ can be moved along any direction $dx_m$ without changing its perceived direction and length. As shown in the next paragraph, $\Gamma_{lm}^k$ can be used to calculate how the observer will describe any evolving stimulus in relative terms: i.e. in terms of a reference stimulus and any two reference transformations. In this sense, the affine connection provides a relativistic description of an observer's perceptual experience. Two observers will consistently have identical perceptual experiences if and only if their affine connections are identical. Experimental methods for measuring the affine connection of an observer are described in Section III hereinafter.

Figure 2:
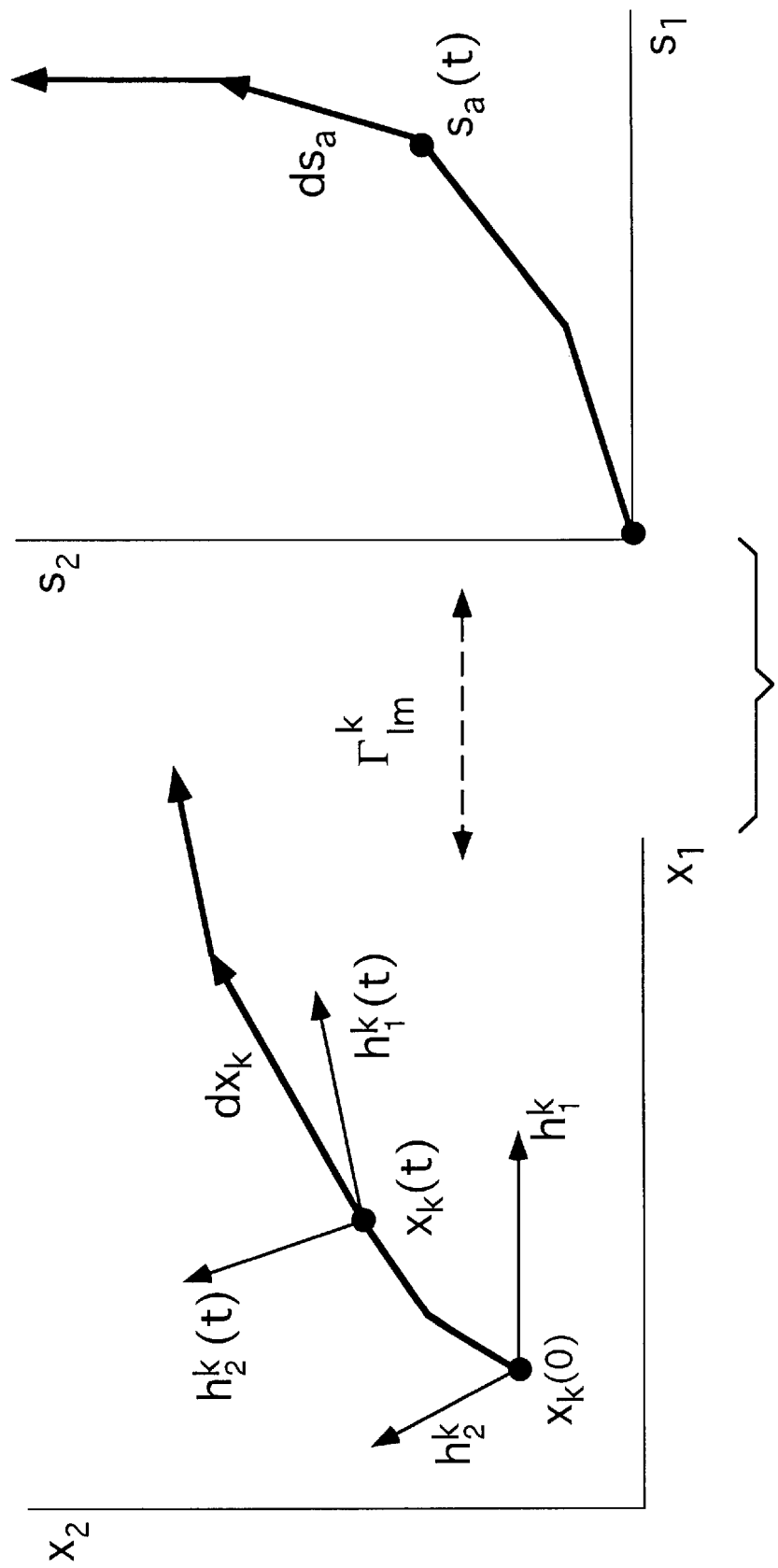
FIG. 2. An evolving stimulus can be described in a coordinate-independent manner as a sequence of transformations that are combinations of reference transformations. Each increment $dx_k$ of the stimulus trajectory $x_k(t)$ can be decomposed into components $ds_a$ along transformations $h_a^k(t)$ of $x_k(t)$ that are perceived to be equivalent to reference transformations $h_a^k$ of the initial stimulus $x_k(0)$. The function $s_a(t)$ describes the course of the evolving stimulus in terms of a series of transformations that are combinations of the reference transformations or their perceptual equivalents. The affinity $\Gamma_{lm}^k$ connects the coordinate-dependent and coordinate-independent descriptions.

Consider the way the observer will describe the evolving stimulus represented by the trajectory $x_k(t)$, where t is a parameter with the range $0 \leq t \leq 1$ (FIG. 2). Suppose that the observer chooses to describe his/her perceptual experience in terms of the reference stimulus at $x_k(0)$ and in terms of two reference transformations at that point, $h_a^k$ where a=1, 2. As in the examples described in the background of the invention (Section I), the observer will witness a series of infinitesimal transformations $dx_k$, each of which can be described as a linear superposition of transformations perceptually equivalent to the reference transformations. In mathematical terms, the infinitesimal transformation $dx_k$ at $x_k(t)$ can be described in terms of its components $ds_a$ along the transformation vectors $h_a^k(t)$ that are perceptually equivalent to the reference transformations $h_a^k$ at $x_k(0)$ $$dx_k = h_1^k(t) ds_1 + h_2^k(t) ds_2 \quad \text{Eq. (2)}$$

Figure 3A:
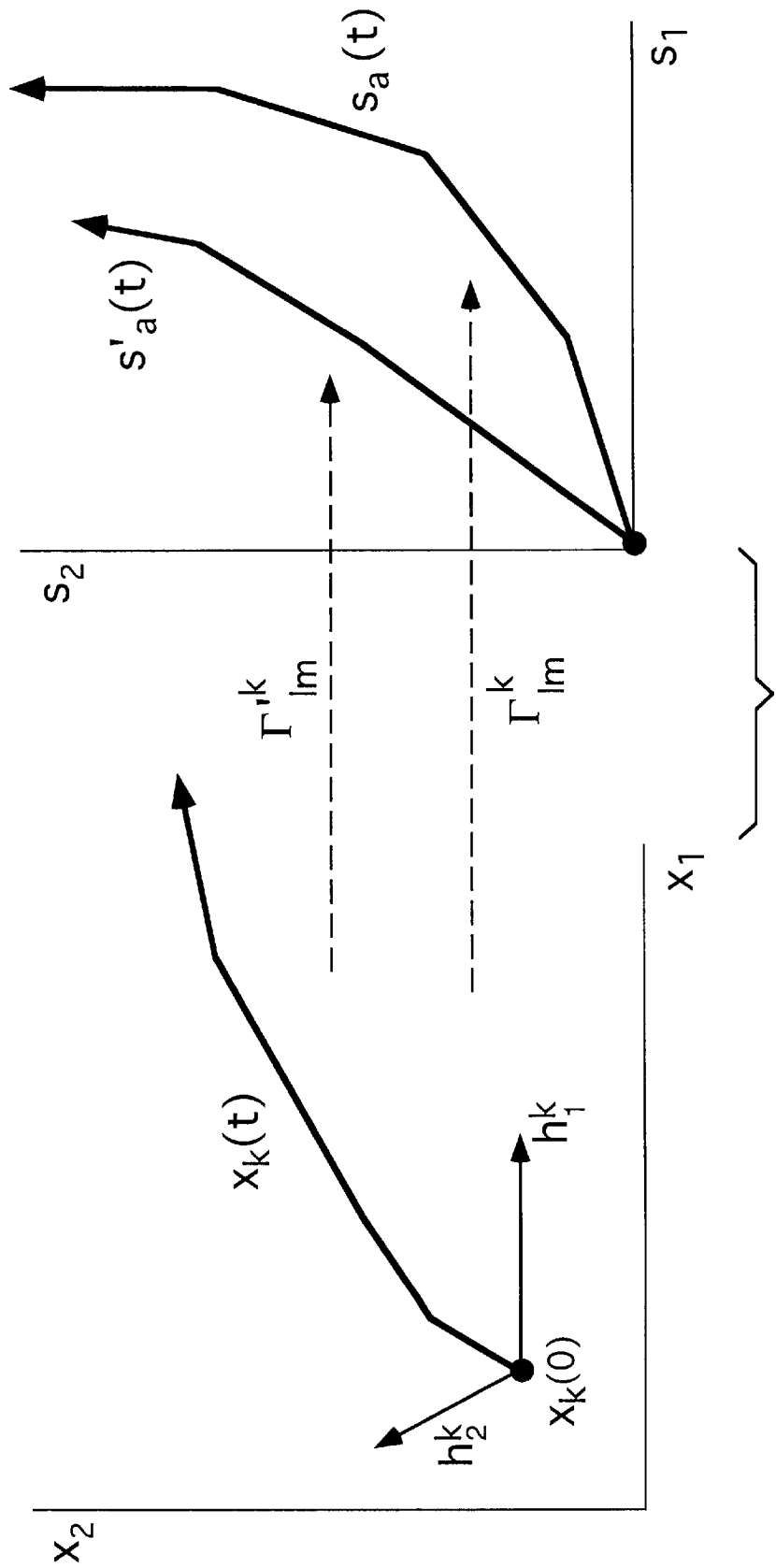
FIG. 3. (a) The perceptual experiences of two observers of the same stimulus $x_k(t)$ can be compared by comparing their coordinate-independent descriptions, $s_a(t)$ and $s_a'(t)$, derived from the common reference transformations $h_a^k$ and each individual's affine connections ($\Gamma_{lm}^k$ and $\Gamma_{lm}^{k'}$). (b) The affine connections of the observers can be used to calculate evolving stimuli, $x_k(t)$ and $x_k'(t)$, that they perceive to result from the same sequence of transformations $[s_a(t)]$.

The function $s_a(t)$, which is constructed by integrating $ds_a$, describes the observer's perceptions in a manner that is independent of the x-coordinate system used to parameterize the stimulus manifold. This is because $s_a(t)$ describes the stimulus solely in terms of other perceptual experiences of the same observer; i.e. in terms of the reference transformations of the reference stimulus. As shown in FIG. 3a, this technique can be used to compare the perceptual experiences of two observers. If they describe the phenomenon with identical functions $s_a(t)$, they will perceive the evolving stimulus to be the result of the same sequence of the same transformations, starting with the same initial stimulus state. If these functions are not identical, the two observers must have utilized different transformations as the local equivalents of the reference transformations. In other words, the two observers perceived different equivalency relations, corresponding to different affine connections. For example, the two observers of the map stimulus in Section I must have had different perceptions of the east/west direction at the location northwest of the Hancock Building.

Referring now to FIG. 2, in principle, the coordinate-independent description $s_a(t)$, of a trajectory $x_k(t)$ can be calculated exactly in terms of the affine connection, taken together with the reference transformations (FIG. 2). Once the $\Gamma_1^k$ of an observer has been measured, Eq.[1] can be used to calculate the $h_a^k(t)$, the transformations perceived to be equivalent to the reference transformations at each point along the trajectory $x_k(t)$. Then, each incremental stimulus transformation can be decomposed in order to derive $s_a(t)$ as in Eq.[2]. As shown in the section entitled "Derivation of the Equations, the function $h_a^k(t)$ must be found by solving an integral equation in which $\Gamma_{lm}^k$ is the kernel. Although this equation cannot be solved exactly, it can be used to develop a perturbative solution for $h_a^k(t)$ which is valid for trajectories $x_k(t)$ in a sufficiently small neighborhood of $x_k(0)$. The first three terms in the corresponding perturbative solution for $s_a(t)$ are derived in the Derivation of the Equations section.

$$s_a(t) = \sum_{k=1,2} h_{ka}[x_k(t) - x_k(0)] - \quad \text{Eq. (3)}$$

$$\sum_{k,l,m=1,2} \Gamma_{lm}^k h_{ka} \int_0^t [x_j(u) - x_l(t)] \frac{dx_m}{du} du -$$

$$\sum_{i,j,k,l,m=1,2} \left[ \frac{\partial \Gamma_{lm}^k}{\partial x_i} + \Gamma_{lm}^j \Gamma_{ji}^k \right] h_{ka} \int_0^t [x_l(u) -$$

$$x_l(t)][x_i(u) - x_i(0)] \frac{dx_m}{du} du$$

Here, the affine connection and its derivatives are evaluated at the origin of the trajectory $x_k(0)$, and $h_{ka}$ is the inverse of the matrix defined by the reference transformations: i.e. $h_{l1} h_1^k + h_{l2} h_2^k = \delta_l^k$, where $\delta_l^k$ denotes the Kronecker delta. The expression in Eq.[3] does not account for terms which are quartic and higher order in $[x_k(t)-x_k(0)]$; therefore, it is only accurate for trajectories in small neighborhoods of the reference point.

Given an observer's affine connection and his/her choices of the reference stimulus and reference transformations, one can calculate the stimulus trajectory $x_k(t)$ corresponding to a given coordinate-independent description $s_a(t)$. In other words, the relationship in Eq.[3] can be inverted (FIG. 2). The perturbative form of this inverse relationship is $$x_k(t) = x_k(0) + \sum_{a=1,2} h_a^k s_a(t) + \quad \text{Eq. (4)}$$

$$\sum_{l,m,a,b=1,2} \Gamma_{lm}^k h_a^l h_b^m \int_0^t [s_a(u) - s_a(t)] \frac{ds_b}{du} du +$$

$$\sum_{i,j,l,m,a,b,c=1,2} \left[ \frac{\partial \Gamma_{lm}^k}{\partial x_i} - \Gamma_{jm}^k \Gamma_{li}^j - \Gamma_{ij}^k \Gamma_{mi}^j \right] h_a^l h_b^i h_c^m \int_0^t [s_a(u) -$$

$$s_a(t)] s_b(u) \frac{ds_c}{du} du$$

Here, the affine connection and its derivatives are evaluated at the origin of the trajectory $x_k(0)$. Since Eq.[4] was derived by ignoring quartic and higher order terms in $[x_k(t)-x_k(0)]$, it is only valid for trajectories in the neighborhood of the reference point $x_k(0)$.

Figure 3B:
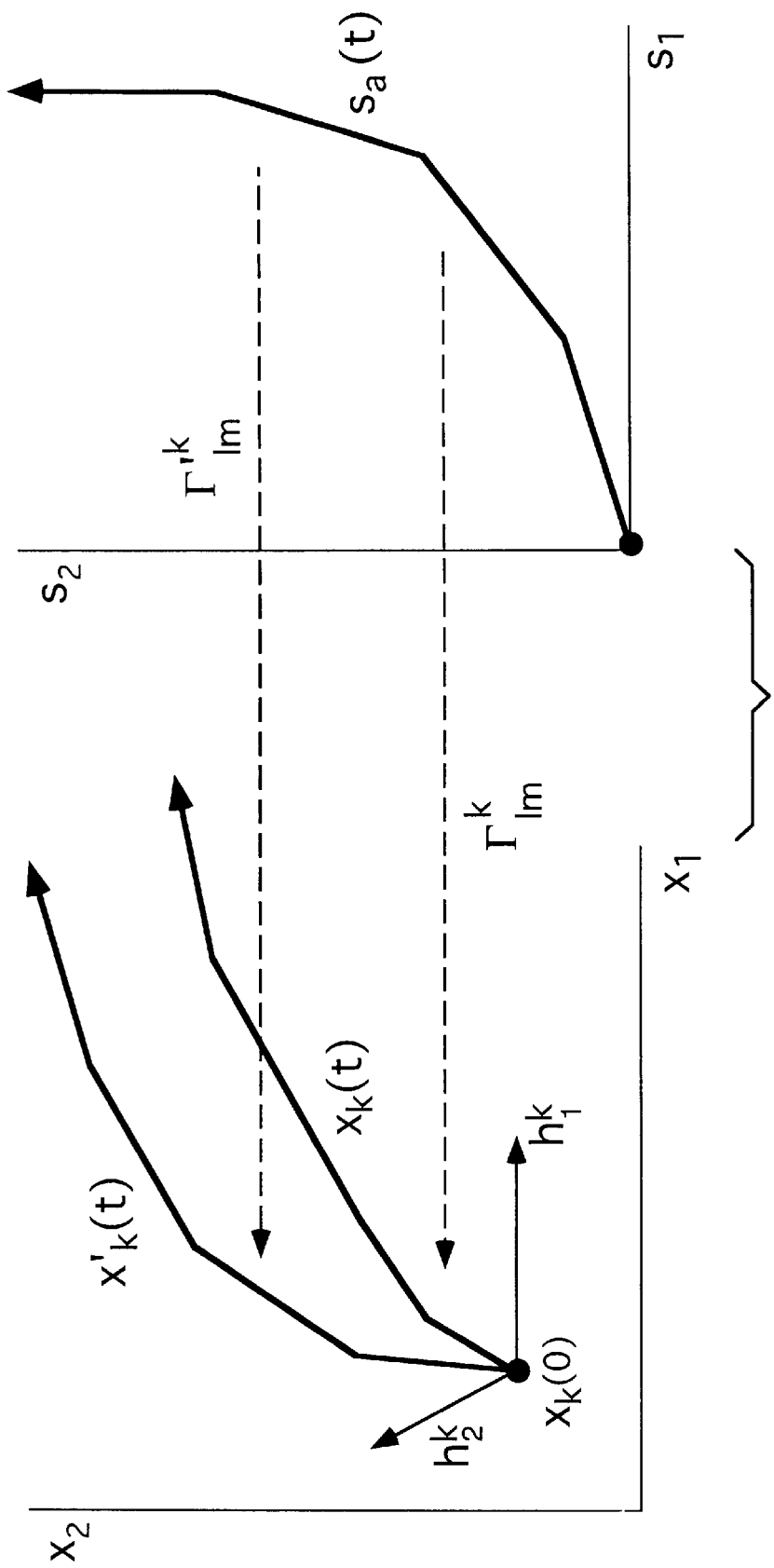

As shown in FIG. 3b, this equation can be used to find different stimuli that two observers having different affine connections will describe in the same way in terms of applications of the same transformations, starting with the same initial stimulus state. Taken together, Eqs. 3 and 4 can be used to map a stimulus perceived by one observer onto another stimulus, perceived in the same way by another observer.

There is a particularly simple interpretation of a trajectory $x_k(t)$ corresponding to a coordinate-independent description $s_a(t)$ that is a straight line. This type of evolving stimulus is perceived to be the result of repeated applications of the same transformation. For example, the trajectory $x_k(t)$, generated by substituting the straight line $s_a(t) = t \delta_a^{\ 1}$ into Eq.[4], is created by repeated applications of transformations perceptually equivalent to $h_1^k$. For example, this might correspond to the highest note of a musical chord being transformed repeatedly to a higher and higher pitch. Such trajectories, which are the analogs of "straight lines" in the observer's perceptual space, are the geodesics of differential geometry.

B. Flat Perceptual Spaces with Symmetric Connections

Referring now to FIG. 4, consider a perceptual space which has the following intrinsic property: every trajectory forming a simple closed loop corresponds to a coordinate-independent description which also forms a simple closed loop (FIG. 4). This implies that the integral of the incremental transformations perceived by the observer vanishes when the stimulus returns to its initial state. In other words, the observer perceives no net change when there has been no net change in the physical state of the stimulus. This condition can be restated in another way: any two trajectories, $x_k(t)$ and $x_k'(t)$, with the same endpoints (stimuli A and B) correspond to two coordinate-independent descriptions, $s_a(t)$ and $s_a'(t)$, with identical endpoints (FIG. 4). In other words, if a stimulus evolves in two different ways from state A to state B, the net transformations perceived by the observer are identical. This means that the observer perceives the same net change no matter how the stimulus evolves between given initial and final states. The perceptual experiences of most normal observers commonly have this type of self-consistency, at least to a good approximation. For example, most observers perceive the same net change in a face whether the observed face: 1) first undergoes a right eye movement and then a left eye movement, or 2) first undergoes the same physical movement of the left eye, followed by the same physical movement of the right eye. Manifolds with this property have the following feature: because the net change in $s_a$ between any two stimuli is independent of the path between them, each stimulus state can be assigned a value of $s_a$ with respect to some fixed reference stimulus. In other words, the perceived transformations relating each state to the reference state can be used to establish a "natural" coordinate system with the reference stimulus at the origin. Then, the relative coordinates of two stimuli can be used to characterize all possible sequences of transformations leading from one to the other. For example, if the observer sees a face with one eye closed e.g. the right eye), he/she immediately knows the transformations necessary to change that face into one with the opposite eye closed: namely, a left eye closure transformation and a right eye opening transformation, performed in any order. Thus, the existence of this natural coordinate system makes it easy for the observer to "navigate" among perceived stimuli "without getting lost".

In the language of differential geometry, such a manifold must be intrinsically flat and have a symmetric affine connection; namely, $$B_{lmn}{}^k(x)=0$$
$$V^k(x)=0 \quad \text{Eq. (5)}$$

where $B_{lmn}{}^k$ is the Riemann-Christoffel curvature tensor $$B_{lmn}^k = -\frac{\partial \Gamma_{lm}^k}{\partial x_n} + \frac{\partial \Gamma_{ln}^k}{\partial x_m} + \sum_{i=1,2}(\Gamma_{im}^k \Gamma_{ln}^i - \Gamma_{in}^k \Gamma_{lm}^i) \quad \text{Eq. (6)}$$

and $V^k$ is the anti-symmetric part of the affine connection $$V^k = \Gamma_{12}{}^k - \Gamma_{21}{}^k \quad \text{Eq. (7)}$$

Since the curvature tensor is antisymmetric in the last two covariant indices, its only independent components are $B_{l12}{}^k$ on a two dimensional manifold. This object transforms as a mixed tensor density. Manifolds with flat symmetric affinities have the property that there are special "geodesic" coordinate systems in which the affine connection vanishes everywhere and in which all geodesic trajectories are straight lines. In fact, these are the above-mentioned $s_a$ coordinate systems in which the coordinates of each stimulus state directly correspond to the perceived transformations leading to that state.

Figure 5:
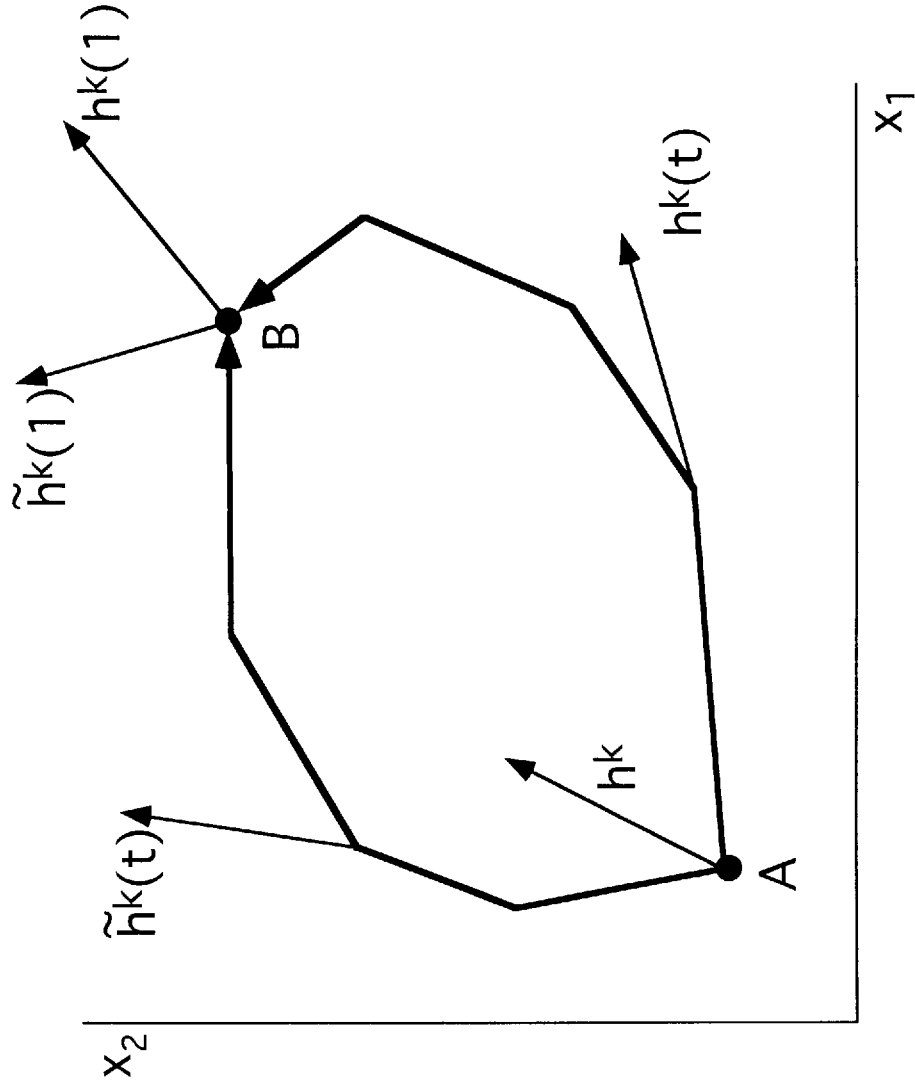
FIG. 5. For a curved manifold, the transformations at B, $h^k(1)$ and $\bar{h}^k(1)$ that are perceptually equivalent to a reference transformation $h^k$ at A, may depend on the path taken from A to B. For flat manifolds, there is only one equivalent transformation: $h^k(1)=\bar{h}^k(1)$.

Referring now to FIG. 5, flat manifolds have another important property: the transformation of stimulus B that is perceived to be equivalent to a given transformation of A is independent of the configuration of the trajectory taken from A to B. This corresponds to the condition $h^k(1)=\bar{h}^k(1)$ in FIG. 5. Thus, the observer always equates the same transformation at B to a given transformation at A, no matter what sequence of transformations led to B. In other words, the observer can navigate among the stimuli of the manifold without losing his "bearings" or becoming perceptually disoriented. The observer might be able to do this by using information intrinsic to the stimulus to deduce equivalent transformations at each point on the manifold. In the map example in Section I, this would be the case if a small compass symbol were printed at each location on the map.

Flat perceptual spaces can be characterized by functions that are simpler than the affine connection. Given any set of reference transformations $h_a{}^k$ of a reference stimulus, the observer can identify perceptually equivalent transformations of other stimuli with various coordinates $(x_k)$. Because the transformations identified at each point do not depend on the path leading from the reference stimulus to that point, they are well-defined functions of the point's coordinates $x_k$; i.e. they can be written as $h_a{}^k(x)$. It can then be shown that the affine connection can be written in terms of these functions and their inverses:

$$\Gamma_{lm}^k(x) = -h_{l1}(x)\frac{\partial h_1^k}{\partial x_m} - h_{l2}(x)\frac{\partial h_2^k}{\partial x_m} \quad \text{Eq. (8)}$$

In other words, the eight components of the affinity can be expressed in terms of two functions, each of which has two components. In practice, if the values of $h_a{}^k(x)$ are measured for stimuli at a dense enough collection of points in the manifold, values of $h_a{}^k(x)$ at other points can be estimated by interpolation (e.g. by fitting the measured values to a parametric form such as a Taylor series or by using a suitably trained neural network).

C. Perceptual Spaces with Curvature and/or Asymmetric Connections

Figure 6:
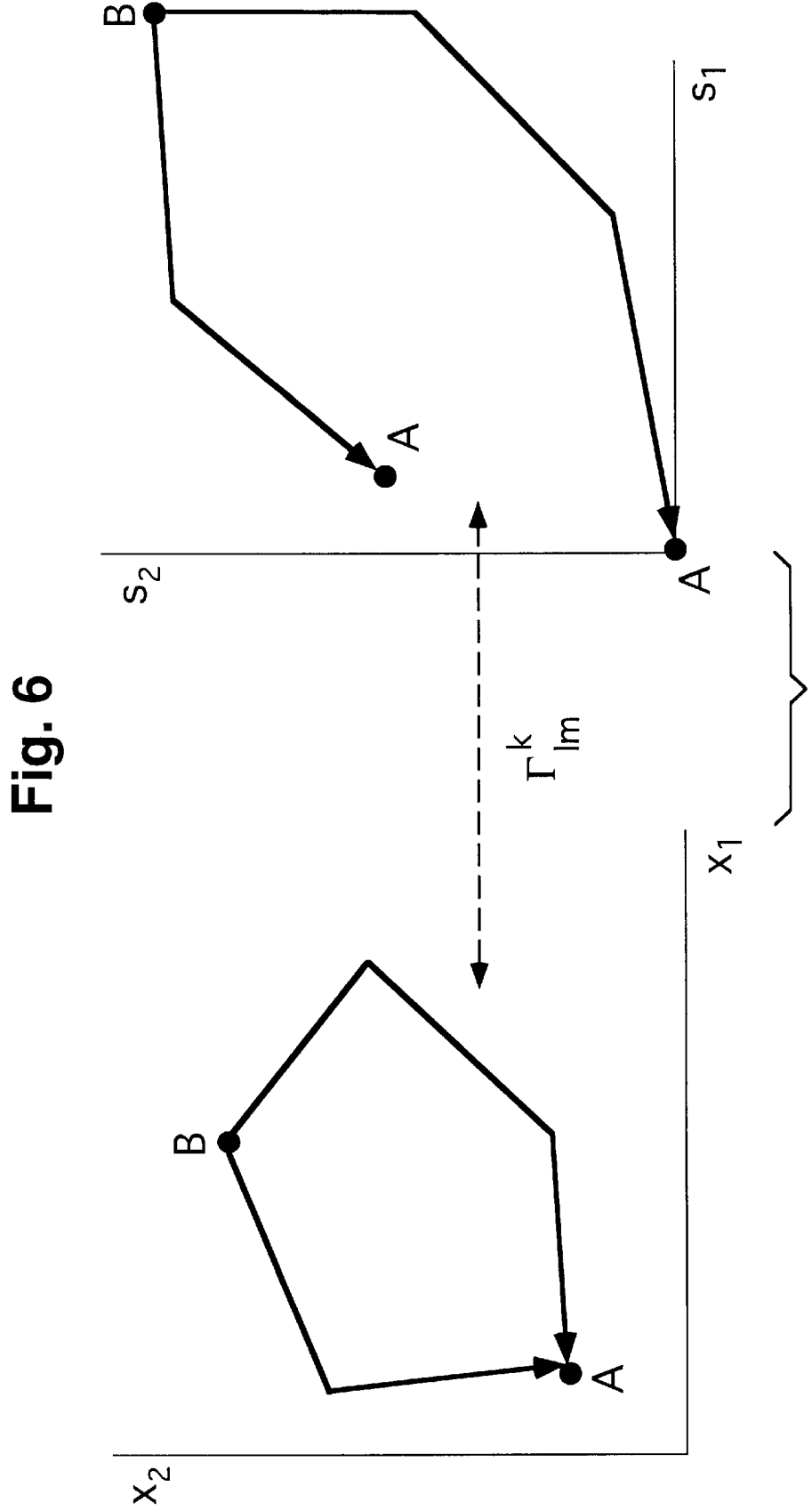
FIG. 6. If the affine connection is curved and/or asymmetric, some loop-like trajectories (left panel) will have coordinate-independent descriptions (right panel) that do not return to the initial point. Therefore, if the stimulus evolves from any point on the trajectory (point B) to the initial point on the trajectory (point A), the net transformation perceived by the observer depends on which limb of the trajectory was followed.

Referring now to FIG. 6, if $B_{lmn}{}^k$ does not vanish everywhere, the manifold is said to have intrinsic curvature. This means that the observer's perceptual system has the following intrinsic property (FIG. 6): some loop-like trajectories $x_k(t)$ correspond to coordinate-independent descriptions $s_a(t)$ which are open curves. Therefore, if the stimulus evolves from any point on the trajectory (point B) to the initial point on the trajectory (point A), the net transformation perceived by the observer depends on which limb of the trajectory was followed. This means that each stimulus cannot be unambiguously identified by the net perceived transformations relating it to a fixed reference stimulus. In other words, the $s_a$ values perceived by the observer cannot be used to establish a coordinate system on the manifold. A confusing situation may develop if the observer is not cognizant of the manifold's curvature: the perception of a stimulus may depend on the configuration of the trajectory leading to it. Thus, if the same physical stimulus A is observed on two different occasions separated by observations of other stimuli, the observer may perceive that there has been a net change in A (FIG. 6); he/she may not even recognize A. An analogous problem would occur if one tried to use the navigational rules of flat space to navigate on the surface of a sphere. For example, consider a trajectory on a sphere consisting of the following movements: an initial movement along a great circle by one quarter of the circumference, followed by a leftward movement along the locally orthogonal great circle by one-quarter of the circumference, followed by a similar leftward movement along the locally orthogonal great circle. This describes a "round-trip" journey which takes the traveler back to the starting point on the sphere. However, if the journey is interpreted with flat space perceptions, it will be perceived as having an "open leg". Therefore the "flat-minded" traveler may not recognize that the starting point has been revisited. Alternatively, if the traveler has memories of the starting point, his/her perceptions of the journey will conflict with those memories. Of course, if the curvature is explicitly taken into account, it is possible to navigate accurately, i.e. to have consistent, reproducible perceptions of evolving stimuli.

Curved perceptual spaces have another potentially problematical property: the transformation of stimulus B, which is perceived to be equivalent to a given transformation of A, depends of the configuration of the trajectory taken from A to B. This corresponds to the condition $h^k(1) \neq \tilde{h}^k(1)$ in FIG. 5. In contrast to flat perceptual spaces, there is no unambiguous, path-independent choice of an equivalent transformation. Therefore, the observer's perception of the transformation of a stimulus is dependent on the history to the transformations used to reach the stimulus state. This will not confuse an observer who is aware of the space's curvature and accounts for it. However, inconsistent perceptions will occur if the observer erroneously assumes that the perceptual space is flat. For example, if the "flat-minded" traveler on a sphere revisits a point at which directional conventions were originally established, he/she may fail to identify those directions correctly.

Perceptual problems can also arise if the curvature tensor vanishes, but the affine connection is asymmetric; i.e. if the first part of Eq.[5] is true, but the second part is not. In this case, it can be shown that the observer's perception of the net transformation between two stimuli is dependent on the trajectory of stimulus evolution between those points (FIG. 6). Thus, just as in curved spaces, the observer's perceptions of transformations cannot be used to establish a coordinate system on the manifold. The naive observer, who is unaware of the asymmetry of the connection, will perceive confusing relationships between different stimuli as in the case of a curved space. On the other hand, since the curvature is zero, the observer's perceptions do suffice to define equivalent "local" transformations in an unambiguous fashion. Therefore, even the naive observer will be able to recognize previously-encountered transformations upon revisiting a stimulus; i.e. the observer will not suffer from the sense of disorientation possible in curved spaces.

III. Methods and Apparatus

A. Components of the Apparatus

Figure 7:
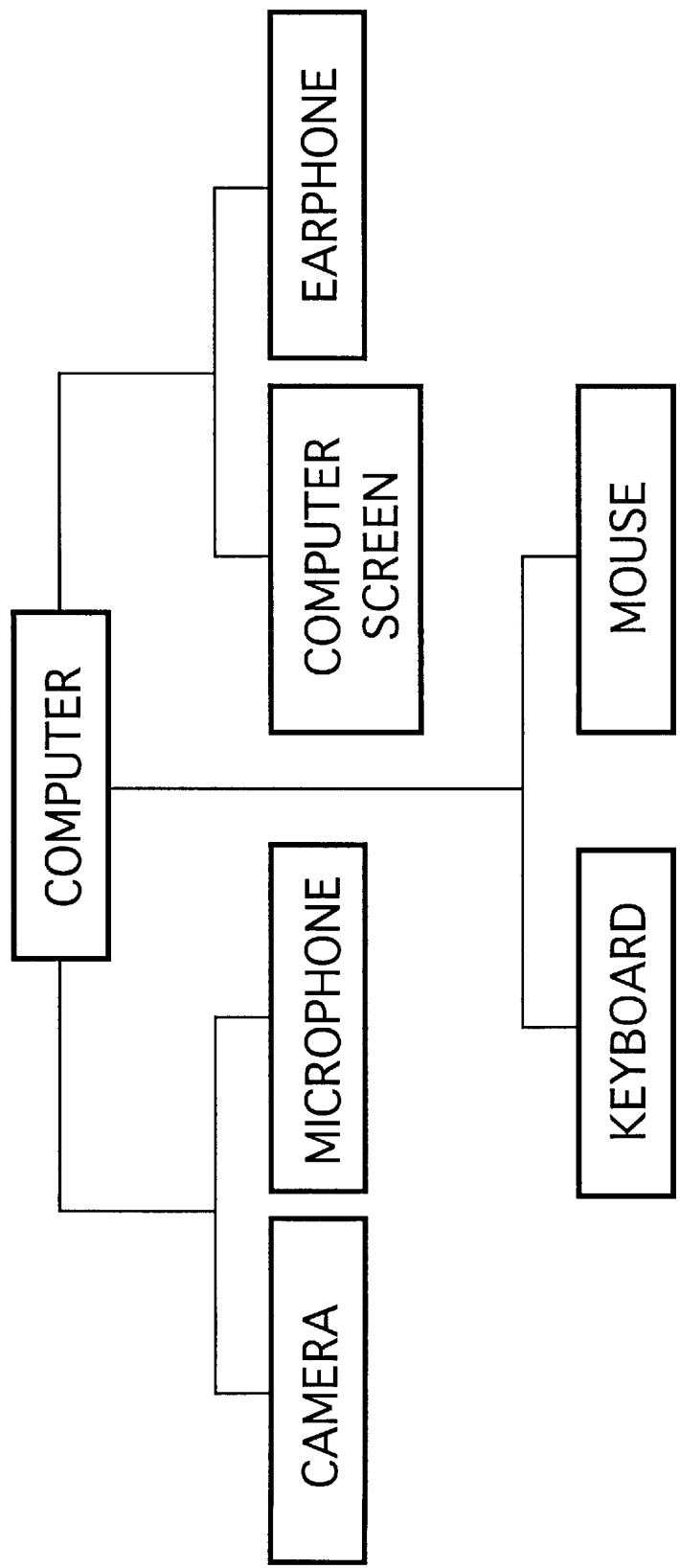
FIG. 7. The components of the apparatus include a computer, stimulus recording devices such as a camera and a microphone, stimulus presentation devices such as a computer screen and earphones, and stimulus manipulation devices such as a keyboard and a mouse.

The apparatus for measuring, characterizing, comparing, emulating, and transducing the perception of observers, according to a specific embodiment includes a computer, stimulus recording devices, stimulus presentation devices, stimulus manipulation devices, and software (FIG. 7). Note that the "observers" are human beings or machines that sense and describe stimuli in terms of other stimuli.

1. Computer

In one specific embodiment, this includes a personal computer or a computer workstation or a mainframe computer. It is equipped with a central processing unit, an operating system, and memory devices (semiconductor memory chips, magnetic disks, magnetic tapes, optical disks).

2. Stimulus Recording Devices (a) Visual stimuli are recorded by imaging devices such as video cameras, CCD cameras, optical photographic equipment, optical microscopes, infrared cameras, microwave detectors (e.g. radar), x-ray detectors (e.g. radiography, computed tomography), radio signal detectors (e.g. MRI), radioactivity detectors (e.g. scintillation cameras), electron microscopes, and ultrasonic detectors (sonar, medical ultrasonic scanners). The resulting signals are digitized, transferred to the computer, and stored as digital image files.

(b) Auditory stimuli are recorded by microphones, and then they are digitized, transferred to the computer, and stored as digital sound files.

3. Stimulus Presentation Devices (a) Visual stimuli are presented on a computer monitor or on a television screen or by an immersive display (e.g. head-mounted display, steerable "boom" display, room-sized display surrounding the observer) or as holographic images.

(b) Auditory stimuli are presented through ear phones or loudspeakers.

(c) A stimulus can have both visual and auditory components.

4. Stimulus Manipulation Devices

This is a keyboard, a 2D digitizing system (e.g. a mouse), a 3D digitizing system attached to parts of the observer's body, a data glove, or a microphone with a voice recognition system that the observer can use to change the presented stimulus. For example, a movement of a mouse might cause a change in the color and/or intensity of a visual stimulus or might cause a change in the pitch and/or intensity of an auditory stimulus.

5. Stimulus Database

The memory devices contain a collection of digital files of recorded or synthetic stimuli. Each stimulus is assigned unique coordinate values $x_k=(x_1, x_2, \ldots, x_N)$ that are stored in the database with that file. These coordinates are assigned so that small incremental coordinate changes correspond to small changes of the parameters controlling the presentation of the stimulus by the stimulus presentation device. For example, the stimulus database with N=2 might consist of digital images, each of which is a uniform array of two numbers, x1 and x2, assigned to each pixel. When the stimulus is sent to a computer screen (the stimulus presentation device), the coordinates x1 and X2 would control the screen's "red" and "blue" channels, respectively.

6. Parallel Transporter

Figure 8:
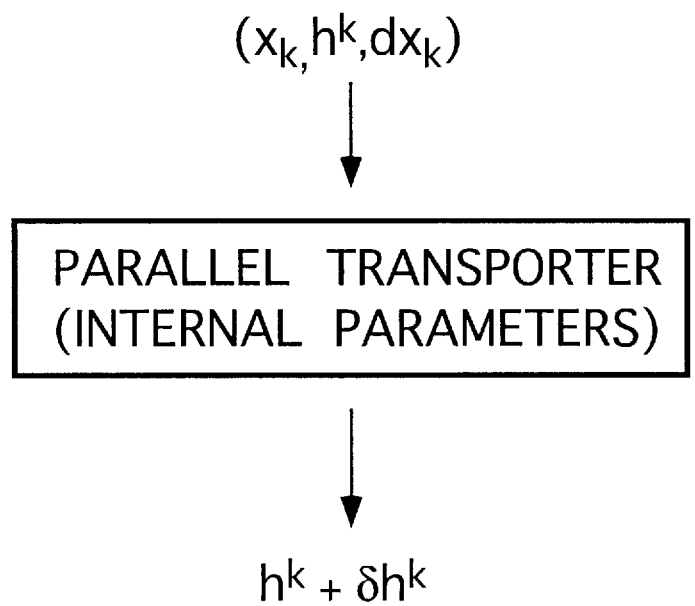
FIG. 8. The parallel transport component maps the coordinates $x_k$ of a stimulus, a vector $h^k$ determining a small transformation of that stimulus, and another vector $dx_k$ determining another small transformation of that stimulus onto a vector $h^k+\delta h^k$ determining a small transformation of the stimulus with coordinates $x_k+dx_k$.

The parallel transporter is a component that maps any small transformation of any stimulus in the database onto another small transformation of another stimulus in the database that differs from the first stimulus by any other small transformation (FIGS. 1 and 8). Specifically, let $x_k$ be the coordinates of any stimulus in the database, and let $h^k$ represent any N small numbers. The sequence of stimuli corresponding to the coordinates $x_k+uh^k$, where u varies between 0 and 1, is called a transformation of the stimulus at $x_k$. Let $dx_k$ represent any other N small numbers. The parallel transporter maps the numbers $(x_k, h^k, dx_k)$ onto N numbers denoted by $h^k+\delta h^k$. These determine a sequence of stimuli with coordinates $x_k+dx_k+u(h^k+\delta h^k)$, where u varies between 0 and 1. This sequence represents the transformation of the stimulus with coordinates $x_k+dx_k$, said transformation being the parallel-transported version of the transformation of the stimulus with coordinates $x_k$. For example: the stimulus at $x_k$ may be a uniform blue color, and the transformation of it determined by $h^k$ may make it one shade redder; the stimulus at $x_k+dx_k$ may be a deeper blue than the one at $x_k$, and the transformation of it, determined by $h^k+\delta h^k$, may also make it one shade redder. In general, the operation of the parallel transporter depends on the values of its internal parameters that are determined by means of the training procedure described below. The parallel transporter may be a software program in the system's computer, or it may be embodied in a hardware component of the system.

(a) The parallel transporter may be embodied by a software program for performing the following mapping of ($x_k$, $h^k$, $dx_k$) onto $h^k+\delta h^k$:

$$h^k + \partial h^k = h^k - \sum_{l,m=1,\ldots,N} \Gamma^k_{lm}(x) h^l dx_m \qquad \text{Eq. (9)}$$

(i) In one embodiment, $\Gamma$ is given by the first J terms in a Taylor series expansion $$\Gamma^k_{lm}(x) = \Gamma^k_{lm}(x_0) + \qquad \text{Eq. (10)}$$

$$\sum_{j=1,\ldots J} \frac{1}{j!} \left[ \sum_{n=1,\ldots N} (x_n - x_{0n}) \frac{\partial}{\partial x_n} \right]^j \Gamma^k_{lm}(x)_{x=x_0}$$

The values of the coefficients $\Gamma_{lm}{}^k(x_0)$ and $\partial_{n1} \ldots \partial_{nj}\Gamma_{lm}{}^k x_0)$ are the internal parameters to be determined by the training procedure described below. The values of $x_{0k}$ are chosen to be the coordinates of a convenient stimulus in the database.

(ii) In another embodiment, the function $\Gamma$ in Eq.[9 ] has the "flat" space form $$\Gamma^k_{lm}(x) = - \sum_{a=1,\ldots,N} f_{la}(x) \frac{\partial}{\partial x_m} f_a{}^k(x) \qquad \text{Eq. (11)}$$

where the N functions $f_a{}^k(x)$ for $a=1, \ldots, N$ are given by a Taylor series expansion with J terms $$f_a{}^k(x) = f_a{}^k(x_0) + \qquad \text{Eq. (12)}$$

$$\sum_{j=1,\ldots J} \frac{1}{j!} \left[ \sum_{n=1,\ldots N} (x_n - x_{0n}) \frac{\partial}{\partial x_n} \right]^j f_a{}^k(x)_{x=x_0}$$

where $f_{ka}(x)$ is the inverse of $f_a{}^k(x)$, determined by solving the linear equations $$\sum_{a=1,\ldots N} f_{la}(x) f_a{}^k(x) = \delta_l^k, \qquad \text{Eq. (13)}$$

where $x_{0k}$ are the coordinates of any stimulus in the database, and where $f_a{}^k(x_0)$ are any N linearly independent vectors with indices k and labels $a=1, \ldots, N$. The quantities $\partial_{n1} \ldots \partial_{nj}f_a{}^k(x_0)$ are the internal parameters of the parallel transporter, to be determined by the training procedure described below (iii) In another embodiment, the function $\Gamma$ in Eq.[9] may be embodied as any non-linear function of both $x_k$ and the internal parameters of the parallel transporter.

(b) The parallel transporter may also be embodied as a software or hardware component with the architecture of a neural network that maps the input numbers ($x_k$, $h^k$, $dx_k$) onto the output numbers $h^k+\delta h^k$. The connection strengths (or weights) of the neural network, together with the parameters that determine the characteristics of its nodes, comprise the internal parameters to be determined by the training procedure described below.

Figure 9:
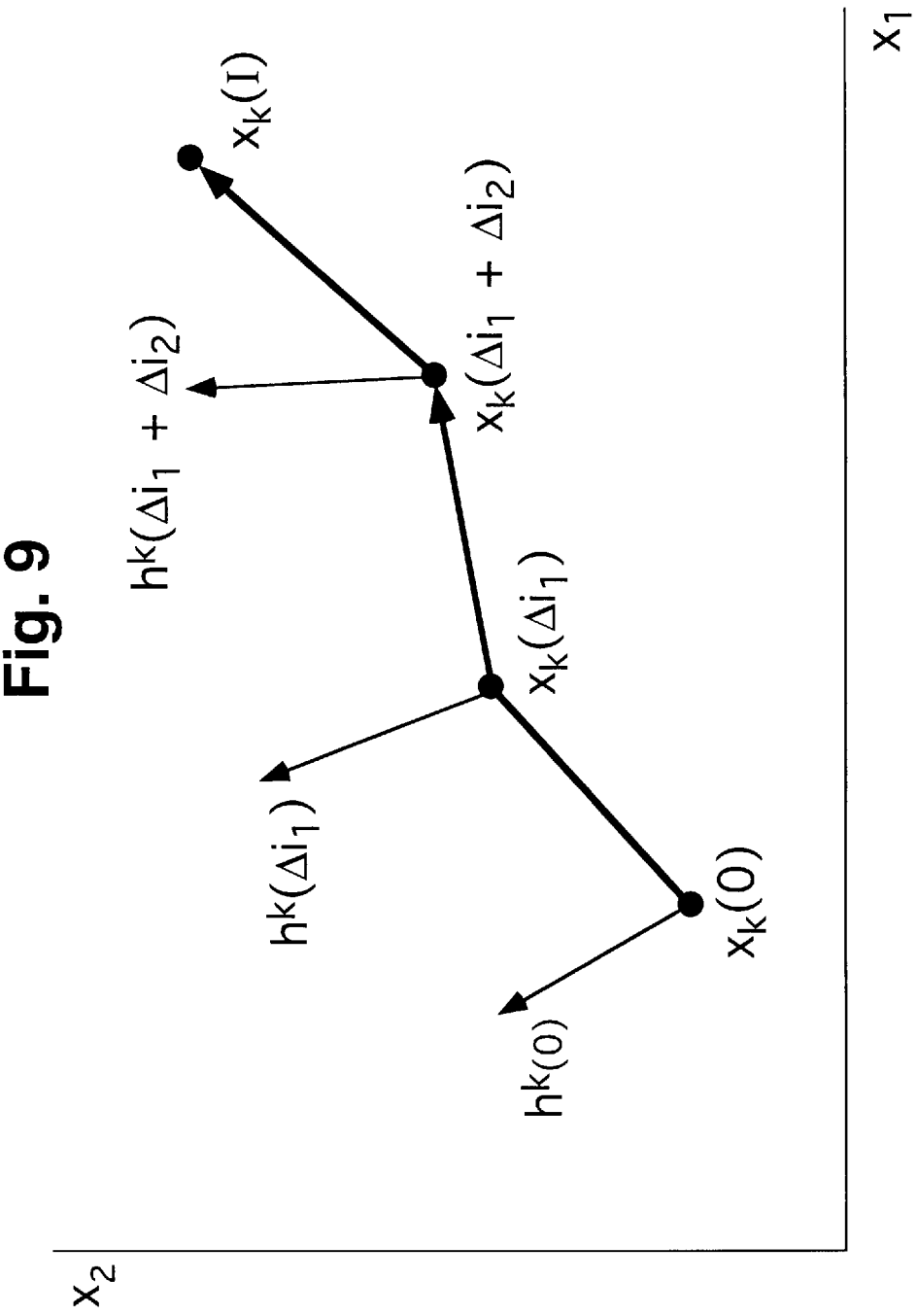
FIG. 9. Measurements of the parallel transport of stimulus transformations, collected from an observer in order to determine the parallel transport component from that observer. At each stimulus with coordinates $x_k(\Delta i)$ in a sequence of stimuli, the observer uses the stimulus manipulation device to find the vector $h^k(\Delta i)$ that determines a small transformation of that stimulus, said transformation being perceptually equivalent to the small transformation of the stimulus with coordinates $x_k(0)$ determined by the vector $h^k(0)$.

B. Determining the Parallel Transporter for an Observer
1. Acquisition of Perceptual Measurements (a) The following data shown in FIG. 9 are collected from the observer whose perception is to be measured, characterized, compared, emulated, or transduced. The first step is the selection of a sequence of stimuli from the database with coordinates given by $x_k(i)$ where i varies between 0 and 1. The observer may operate the stimulus manipulation device to select this sequence of stimuli; alternatively, this sequence of stimuli may be specified by the system's software. This sequence of stimulus coordinates is stored in the memory of the computer. Then, the observer (or the computer program) specifies a small transformation $x_k(0)+uh^k(0)$ of the stimulus with coordinates $x_k(0)$, where u varies from 0 to 1. This transformation is stored in memory by the computer and displayed by the stimulus display device. Then, the observer uses the stimulus manipulation device to display the sequence of stimuli with coordinates $x_k(i)$ for values of i increasing from 0 to a small number $\Delta i_1$ chosen by the observer. Alternatively, the computer may be programmed to choose $\Delta i_1$ and to display this sequence of stimuli. The observer then uses the stimulus manipulation device to find a transformation $x_k(\Delta i_1)+uh^k(\Delta i_1)$ of the stimulus with coordinates $x_k(\Delta i_1)$, that transformation being perceived to be equivalent to the previously displayed small transformation of the stimulus at $x_k(0)$. The coordinates $x_k(\Delta i_1)$ and the numbers $h^k(\Delta i_1)$ are stored in memory by the computer. Next, the observer uses the stimulus manipulation device to display the sequence of stimuli with coordinates $x_k(i)$ for values of i increasing from $\Delta i_1$ to a small number $\Delta i_1+\Delta i_2$, where $\Delta i_2$ is chosen by the observer Alternatively, the computer may be programmed to select $\Delta i_2$ and to display this sequence of stimuli. The observer then uses the stimulus manipulation device to find a transformation $x_k(\Delta i_1+\Delta i_2)+uh^k(\Delta i_1+\Delta i_2)$ of the stimulus with coordinates $x_k(\Delta i_1+\Delta i_2)$, that transformation being perceived to be equivalent to the previously displayed small transformation of the stimulus at $x_k(\Delta i_1)$. The coordinates $x_k(\Delta i_1+\Delta i_2)$ and the numbers $h^k(\Delta i_1+\Delta i_2)$ are stored in the computer's memory. In this way, the observer proceeds through the sequence of stimuli with coordinates $x_k(i)$ until the stimulus at $x_k(l)$ is reached. In the example of stimuli comprised of mixtures of red and blue colors: the stimuli $x_k(i)$ may represent successively deeper shades of blue while the transformations associated with the vectors $h^k(i)$ may make each of these stimuli one shade redder.

(i) In one embodiment of this procedure (FIG. 1), the computer is programmed to select and store in memory the coordinates of multiple stimuli from the database, according to a random method of selection or according to a programmed algorithm. At each of these selected stimuli with coordinates $x_k$, the computer is programmed to select and store in memory multiple pairs of vectors ($h^k$, $dx_k$), according to a random method of selection or according to a programmed algorithm. The apparatus displays the first selected stimulus with coordinates $x_k$ and then displays the transformation corresponding to the sequence of stimuli with coordinates where u increases from 0 to 1. The apparatus then displays the sequence of stimuli corresponding to the coordinates $x_k+tdx_k$, where t increases from 0 to 1. The observer uses the stimulus manipulation device to select a transformation of the stimulus with coordinates $x_k+dx_k$, that transformation being perceptually equivalent to the computer-selected transformation $x_k+uh^k$ of the stimulus with coordinates $x_k$. The observer-selected transformation is then stored in memory by the computer.

Figure 10:
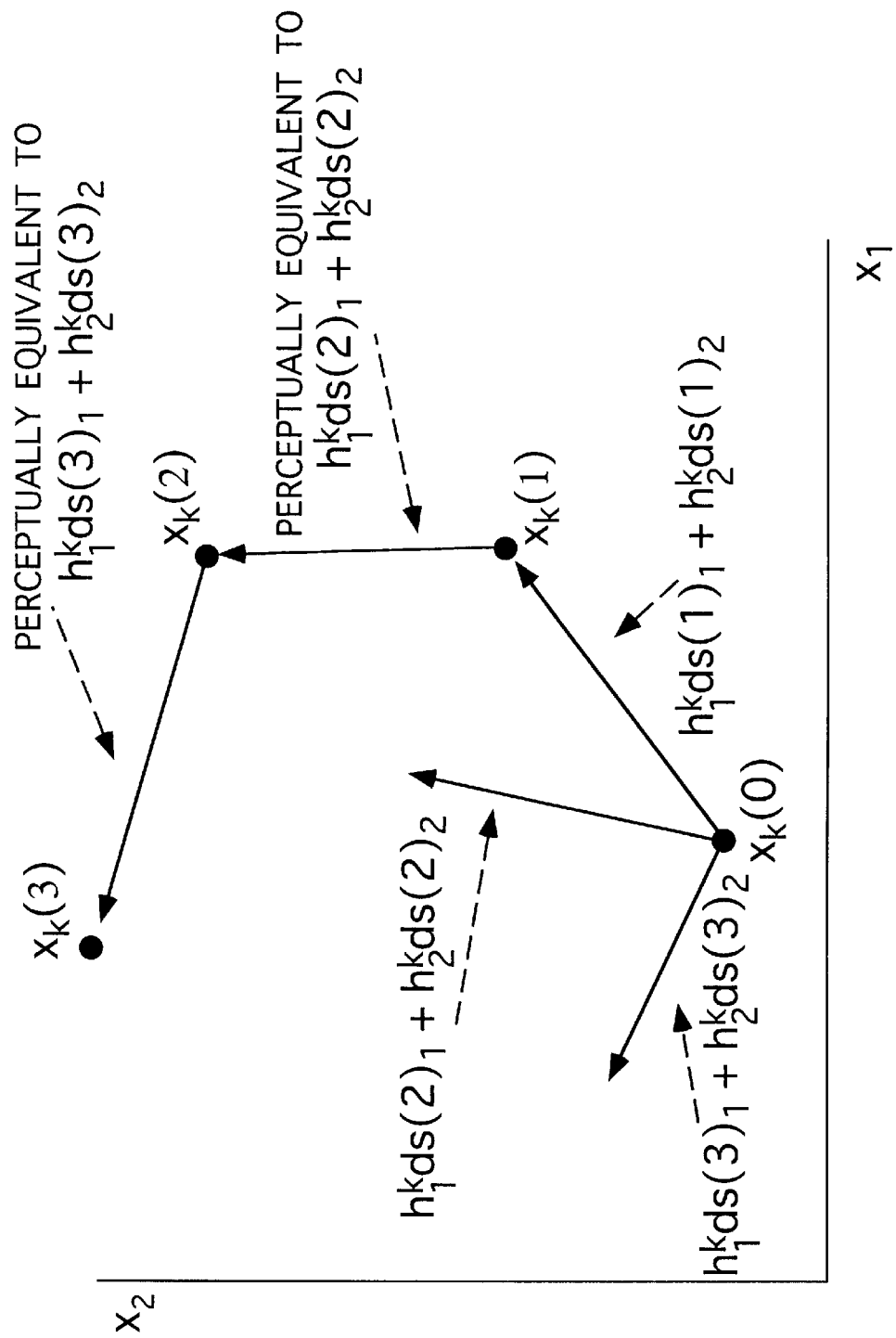
FIG. 10. Trajectory measurements collected from an observer in order to determine the parallel transport component for that observer. Starting with a reference stimulus having coordinates $x_k(0)$, the observer uses the stimulus manipulation device to select a sequence of stimuli, having coordinates $x_k(i)$. The stimuli are chosen so that the $i^{th}$ stimulus differs from the $(i-1)^{th}$ stimulus by a transformation that is perceptually equivalent to a certain weighted sum of reference transformations of the reference stimulus. The reference transformations of the reference stimulus are determined by the vectors $h_a^k$, and their weighting in the transformation from stimulus $i-1$ to stimulus $i$ is given by the numbers $ds(i)_a$.

(b) The following measurements may also be made (FIG. 10). The observer uses the stimulus manipulation device to select a stimulus with coordinates $x_k(0)$ from the stimulus database. Alternatively, this stimulus may be specified in the computer program. The coordinates $x_k(0)$ are stored in the computer's memory. The computer program specifies and stores in memory N linearly-independent vectors $h_a^k$ where the vector label is $a=1, \ldots, N$ and the vector index is $k=1, \ldots, N$. Next, the observer uses the stimulus manipulation device to select a sequence of transformations of the stimulus with coordinates $x_k(0)$, said transformations being given by stimuli with coordinates $$x_k(0) + u \left[ \sum_{a=1,\ldots,N} h_a^k ds(i)_a \right]$$

where u varies from 0 to 1 and i labels the components $ds(i)_a$ of the $i^{th}$ transformation. Alternatively, the computer program specifies this sequence of transformations. The numbers $ds(i)_a$ are stored in the computer's memory. Then, the observer uses the stimulus manipulation device to transform the stimulus with coordinates $x_k(0)$ by the transformation with components $ds(1)_a$. The coordinates $x_k(1)$ of the resulting stimulus are stored in the computer's memory. Then, the observer uses the stimulus manipulation device to transform the resulting stimulus by the transformation perceptually equivalent to the transformation of the stimulus with coordinates $x_k(0)$, said last transformation having components $ds(2)_a$. The coordinates $x_k(2)$ of the resulting stimulus are stored in the computer's memory. Then, the observer uses the stimulus manipulation device to transform the resulting stimulus by the transformation perceptually equivalent to the transformation of the stimulus with coordinates $x_k(0)$, said last transformation having components $ds(3)_a$. The coordinates $x_k(3)$ of the resulting stimulus are stored in the computer's memory. The observer repeats this procedure until he has exhausted the list of transformations with components $ds(i)_a$. The resulting stored stimulus coordinates $x_k(i)$ are said to describe the "trajectory" corresponding to the sequence of transformations with components $ds(i)_a$. This procedure is repeated to generate multiple different trajectories, starting at the stimulus with coordinates $x_k(0)$ and starting with stimuli having other coordinates, chosen as described above. In the example of stimuli consisting of mixtures of red and blue colors: the first and second reference transformations may make the reference stimulus one shade bluer and one shade redder, respectively; as a trajectory is traversed, the stimulus may be perceived to turn one shade redder, followed by one shade bluer, followed by two shades redder, etc.

(i) In one embodiment of this procedure, all of the $ds(i)_a$ in the sequence are the same: $ds(i)_a=(ds_1,\ldots,ds_N)$. The resulting stored coordinates $x_k(i)$ are said to describe a "geodesic" trajectory. In the example of stimuli consisting of mixtures of red and blue colors: a geodesic trajectory would be a series of transformations, each of which makes the stimulus one shade redder.

(ii) In another embodiment, all of the $ds(i)_a$ in the sequence are proportional to one another: $ds(i)_a=ds(i)(ds_1,\ldots,ds_N)$ The observer uses the keyboard to cause the computer to display repetitively the corresponding sequence of stimuli with coordinates $x_k(i)$, at a rate specified in the software. While the sequence is being displayed, the observer manipulates the keyboard and/or the stimulus manipulation device to cause the computer to change the rate at which it subsequently displays those stimuli being displayed at the time of said manipulation. The observer modifies the rate of stimulus display in a repetitive fashion until the displayed stimuli are perceived to be changing at a constant time rate of change. The observer uses the keyboard to cause the computer to store in memory the differences $dt(i)$ between the time of display of each stimulus and time of display of the previous stimulus in the sequence, as well as store in memory the coordinates $x_k(i)$ of all of the stimuli. The stored values of the numbers $ds(i)_a$ are then replaced by the numbers: $ds(i)_a=dt(i)(ds_1,\ldots,ds_N)$. The stored coordinates $x_k(i)$ are also said to describe a "geodesic" trajectory. In the example of stimuli consisting of mixtures of red and blue colors: this type of geodesic trajectory might consist of a series of transformations that consistently make the stimulus redder, but not by the same amount.

(iii) In another embodiment, the numbers $ds(i)_a$ are chosen so that $$\sum_{i=1,2,3\ldots} ds(i)_a = 0.$$

The corresponding values of $x_k(i)$ are said to describe a "perceptual circuit" trajectory. In the example of stimuli consisting of mixtures of red and blue colors: this type of trajectory could consist of four transformations which successively make the stimulus one shade redder, one shade bluer, one shade less red, followed by one shade less blue.

2. Determination of the Internal Parameters of the Parallel Transporter (a) During the measurement procedure in IIIB1a (FIG. 9), the apparatus recorded pairs of transformations, perceived to be equivalent by the observer. Each measurement consists of a transformation $x_k(\Delta i_1 + \ldots + \Delta i_{j+1}) + uh^k(\Delta i_1 + \ldots + \Delta i_{j+1})$ of a stimulus with coordinates $x_k(\Delta i_1 + \ldots + \Delta i_{j+1})$, that transformation being perceived to be equivalent to another transformation $x_k(\Delta i_1 + \ldots + \Delta i_j) + uh^k(\Delta i_1 + \ldots + \Delta i_j)$ of the stimulus with coordinates $x_k(\Delta i_1 + \ldots + \Delta i_j)$. These data are used to determine the values of the parameters in the parallel transporter. Specifically, these parameters are adjusted until the parallel transporter maps the measured values of $(x_k(\Delta i_1 + \ldots + \Delta i_j), h^k(\Delta i_1 + \ldots + \Delta i_j), x_k(\Delta i_1 + \ldots + \Delta i_{j+1}) - x_k(\Delta i_1 + \ldots + \Delta i_j))$ of each pair of measured transformations onto the corresponding measured value of $h^k(\Delta i_1 + \ldots + \Delta i_{j+1})$, with a desired degree of accuracy.

(i) In one embodiment of this process, the parallel transport component is represented in software by Eqs. [9–10]. The measured values of $(x_k(\Delta i_1 + \ldots + \Delta i_j), h^k(\Delta i_1 + \ldots + \Delta i_j), x_k(\Delta i_1 + \ldots + \Delta i_{j+1}) - x_k(\Delta i_1 + \ldots + \Delta i_j))$ and $h^k(\Delta i_1 + \ldots + \Delta i_{j+1})$ are substituted into these equations to derive linear constraints on the internal parameters $\Gamma_{lm}^k(x_0)$ and $\partial_{n1} \ldots \partial_{nj}\Gamma_{lm}^k(x_0)$. Linear regression (Draper, N. R. and Smith, H. Applied Regression Analysis. New York: Wiley, 1981) is used to find the values of the internal parameters that best fit the measurements and to estimate confidence limits for these values.

(ii) In another embodiment of this process, the parallel transport component is represented in software by Eq.[9] and Eqs.[11–13]. The measured values of $(x_k(\Delta i_1 + \ldots + \Delta i_j), h^k(\Delta i_1 + \ldots + \Delta i_j), x_k(\Delta i_1 + \ldots + \Delta i_{j+1}) - x_k(\Delta i_1 + \ldots + \Delta i_j))$ and $h^k(\Delta i_1 + \ldots + \Delta i_{j+1})$ are substituted into these equations to derive non-linear constraints on the internal parameters $\partial_{n1} \ldots \partial_{nj}f_a^k(x_0)$. Non-linear regression (Draper, N. R. and Smith, H. Applied Regression Analysis. New York: Wiley, 1981) is used to find the values of the internal parameters that best fit the measurements and to estimate confidence limits for these values.

(iii) In another embodiment of this process, the parallel transport component is represented in software or hardware by a neural network. The connection strengths and nodal parameters of the neural network are adjusted until it maps each of the measured values of ($x_k$ ($\Delta i_1 + \ldots + \Delta i_j$), $h^k(\Delta i_1 + \ldots + \Delta i_j)$, $x_k(\Delta i_1 + \ldots + \Delta i_{j+1}) - x_k(\Delta i_1 + \ldots + \Delta i_j)$) onto the corresponding measured value of $h^k(\Delta i_1 + \ldots + \Delta i_{j+1})$ with a desired degree of accuracy.

((i)) In one embodiment, the neural network is a back-propagation model.

((ii)) In another embodiment, the neural network is a self-organizing model.

(b) During the measurement process described in IIIB1b (FIG. 10), the observer collected data describing multiple trajectories, each of which is described by trajectory coordinates $x_k(i)$ and associated with a sequence of numbers $ds(i)_a$ and a set of vectors $h_a{}^k$. The internal parameters of the parallel transporter are adjusted, the values of $x_k$ are adjusted, and the values of $ds(i)_a$ are adjusted by i-independent homogeneous affine transformations until the trajectory coordinates $x_k(i)$ are reproduced to a desired degree of accuracy by: 1) $x_k(0)=x_k$, 2) setting $x_k(1)=x_k+dx(1)_k$ where $$dx(1)_k = \sum_{a=1,\ldots,N} h_a{}^k ds(1)_a,$$

3) setting $x_k(2)=x_k+dx(1)_k+dx(2)_k$ where $dx(2)_k$ is obtained by using the parallel transporter to map the numbers ($x_k$, $$\sum_{a=1,\ldots N} h_a{}^k ds(2)_a,$$

$dx(1)_k$) onto $dx(2)_k$, 4) setting $x_k(3)=x_k+dx(1)_k+dx(2)_k+dx(3)_k$ where $dx(3)_k$ is obtained by first using the parallel transporter to map ($x_k$, $$\sum_{a=1,\ldots N} h_a{}^k ds(3)_a,$$

$dx(1)_k$) onto the numbers $dx(3,1)_k$ and then using the parallel transporter to map ($x_k+dx(1)_k$, $dx(3,1)_k$, $dx(2)_k$) onto $dx(3)_k$, 5) continuing in this way to generate stimulus coordinates.

(i) In one embodiment of this process, the parallel transport component is represented in software by Eqs. [9–10], without the terms for j>1 in Eq.[10]. The sequences of coordinates $x_k(i)$ and numbers $ds(i)_a$ for all trajectories, that were measured in IIIB1b, are substituted into the equation $$x_k(i) = x_k + \sum_{a=1,\ldots N} h_a{}^k s_a(i) + \qquad \text{Eq. (14)}$$

$$\sum_{l,m,a,b=1,\ldots N} \Gamma_{lm}^k(x) h_a{}^l h_b{}^m \sum_{j=1,\ldots,i} [s_a(j) - s_a(i)] ds(j)_b +$$

$$\sum_{i',j,l,m,a,b,c=1,\ldots,N} [\partial_{i'} \Gamma_{lm}^k(x_0) - \Gamma_{jm}^k(x_0) \Gamma_{li'}^j(x_0) -$$

$$\Gamma_{ij}^k(x_0) \Gamma_{mi'}^j(x_0)] h_a{}^i h_b{}^{i'} h_c{}^m \sum_{j=1,\ldots,i} [s_a(j) - s_a(i)] s_b(j) ds(j)_c$$

where $$s_a(i) = \sum_{j=1,\ldots,i} ds(j)_a$$

and where $\Gamma_{lm}^k(x)$ is given by Eq.[10] without the terms for j>1. Non-linear regression is used to find the values of the internal parameters $\Gamma_{lm}^k(x_0)$ and $\partial_i \Gamma_{lm}^k(x_0)$, values of $x_k$, and values of the $h_a{}^k$ that satisfy these constraints as well as the constraints $x_k(0)=x_k$, to the desired degree of accuracy.

(ii) Alternatively, a series of linear regression steps is used to derive the internal parameters of the parallel transporter from the measurements in IIIB1b. First, the stimulus coordinates $x_k(i)$ comprising an individual trajectory in IIIB1b are substituted into the left side of the following equation, and the corresponding numbers $ds(i)_a$ are substituted into the right side $$x_k(i) = x_k + \sum_{a=1,\ldots,N} h_a{}^k s_a(i) + \qquad \text{Eq. (15)}$$

$$\sum_{a,b=1,\ldots,N} \beta_{ab}^k \sum_{j=1,\ldots,i} [s_a(j) - s_a(i)] ds(j)_b +$$

$$\sum_{a,b,c=1,\ldots,N} \gamma_{abc}^k \sum_{j=1,\ldots,i} [s_a(j) - s_a(i)] s_b(j) ds(j)_c$$

where $$s_a(i) = \sum_{j=1,\ldots,i} ds(j)_a.$$

Linear regression is used to find the values of $x_k$, $h_a{}^k$, $\beta_{ab}{}^k$, and $\gamma_{abc}{}^k$ that best fit each set of measurements of a single trajectory to these equations and to the equations $x_k(0)=x_k$, with the desired accuracy. The value of $\Gamma_{lm}^k(x(0))$ is derived by using linear regression to best fit the following equation to the values of $h_a{}^k$ and $\beta_{ab}{}^k$ derived in this manner from the set of all of the trajectories initiated at the single stimulus with coordinates $x_k(0)$.

$$\beta_{ab}{}^k = \Gamma_{lm}^k(x(0)) h_a{}^l h_b{}^m \qquad \text{Eq. (16)}$$

The derived values of $\Gamma_{lm}^k(x(0))$ at all of the different values of $x_k(0)$ are substituted into Eq.[10] without terms for j>1 in order to derive linear constraints on $\Gamma_{lm}^k(x_0)$ amd $\partial_i \Gamma_{lm}^k(x_0)$. Linear regression is applied to these equations in order to derive values of the internal parameters $\Gamma_{lm}^k(x_0)$ and $\partial_i \Gamma_{lm}^k(x_0)$ that best fit these data.

(iii) In another embodiment of this process, the parallel transport component is represented in software by Eq.[9] and Eqs.[11–13], omitting all terms in Eq.[12] with j>2. All sets of trajectory measurements $x_k(i)$ and $ds(i)_a$ in IIIB1b are substituted into Eq.[14]. Non-linear regression is used to find the values of the internal parameters, $\partial_i f_a{}^k(x_0)$ and $\partial_i \partial_m f_a{}^k(x_0)$, as well as values of $x_k$ and $h_a{}^k$, so that Eq.[14], Eqs.[11–13] and the equations $x_k(0)=x_k$ are satisfied to a desired degree of accuracy.

(iv) In another embodiment of this process, the parallel transport component is represented in software by Eq.[9] and Eqs.[11–13], omitting all terms in Eq.[12] with j>2. The measurements $x_k(i)$ and $ds(i)_a$ for a single trajectory in IIIB1b are substituted into Eq.[15]. Linear regression is used to find the values of $x_k$, $h_a{}^k$, $\beta_{ab}{}^k$, and $\gamma_{abc}{}^k$ that best fit the measurements of each individual trajectory to these equations and to the equations $x_k(0)=x_k$ with the desired accuracy. The value of $\Gamma_{lm}^k(x(0))$ is derived by using linear regression to best fit Eq.[16] to the values of $h_a{}^k$ and $\beta_{ab}{}^k$ derived in this manner from the set of all trajectory measurements initiated at the single stimulus with coordinates $x_k(0)$. The derived values of $\Gamma_{lm}^k(x(0))$ at all of the values of $x_k(0)$ are substituted into Eq.[10] without terms for j>1 in order to derive linear constraints on $\Gamma_{lm}^k(x_0)$ and $\partial_i \Gamma_{lm}^k(x_0)$. Linear regression is applied to these equations in order to derive values of $\Gamma_{lm}^{k}(x_0)$ and $\partial_i\Gamma_{lm}^{k}(x_0)$ that best fit these data. Linear constraints on the internal parameters $\partial_n f_a^{k}(x_0)$ are derived by substituting the resulting values of $\Gamma_{lm}^{k}(x_0)$ and the known values of $f_{ka}(x_0)$ into $$\Gamma_{lm}^{k}(x_0) = - \sum_{a=1,\ldots,N} f_{la}(x_0)\partial_m f_a^{k}(x_0) \qquad \text{Eq. (17)}$$

Linear regression is used to find the values of $\partial_n f_a^{k}(x_0)$ that best fit these constraints. Linear constraints on the internal parameters $\partial_i\partial_m f_a^{k}(x_0)$ are derived by substituting the derived values of $\partial_i\Gamma_{lm}^{k}(x_0)$ and $\partial_n f_a^{k}(x_0)$, as well as the known values of $f_a^{k}(x_0)$ and $f_{ka}(x_0)$, into $$\partial_i\Gamma_{lm}^{k}(x_0) = - \sum_{a=1,\ldots,N} [\partial_i f_{la}(x_0)\partial_m f_a^{k}(x_0) + f_{la}(x_0)\partial_i\partial_m f_a^{k}(x_0)] \qquad \text{Eq. (18)}$$

$$\sum_{a=1,\ldots,N} [\partial_m f_{la}(x_0)f_a^{k}(x_0) + f_{la}(x_0)\partial_m f_a^{k}(x_0)] = 0 \qquad \text{Eq. (19)}$$

(v) In another embodiment of this process, the parallel transporter is a neural network, implemented in hardware or in software, with internal parameters given by connection strengths and nodal parameters. The process described in IIIB2b is applied to all of the trajectory measurements in IIIB1b in order to adjust the internal parameters, to adjust the values of $x_k$, and to adjust the values of $ds(i)_a$ by i-independent affine transformations, until the values of $x_k(i)$ are reproduced to a desired degree of accuracy.

((i)) In one embodiment, the internal parameters are adjusted iteratively in a back-propagation model.

((ii)) In one embodiment, the internal parameters are adjusted iteratively according in a self-organizing model.

C. Characterizing and Comparing the Perceptions of Observers

1. Characterizing the Perception of a Single Observer

An observer's perceptual performance is characterized by the values of the internal parameters of the parallel transport component, said values having been derived from the measurements collected from the observer by any of the methods in IIIB1 and said derivation being performed according to any of the methods in IIIB2.

(a) In one embodiment, multiple sets of measurements are collected from the observer and used to derive a distribution of the values of each internal parameter of the parallel transport component. The mean and standard deviation of these distributions characterize the perceptual performance of the observer.

2. Characterizing the Perceptions of a Group of Observers

The perceptual performance of a group of observers is characterized by the distributions of values of the internal parameters of the parallel transport component, said values having been derived from the measurements collected from each of the observers in the group by any of the methods in IIIB1 and said derivations being performed according to any of the methods in IIIB2.

(a) In one embodiment, the mean and standard deviation of the distribution of the values of each internal parameter of the parallel transport component characterize the perceptual performance of the group.

3. Comparing the Perceptions of Observers (a) The perceptions of two observers can be compared by calculating statistical measures of the differences between the distributions of the values of the internal parameters of the parallel transport components, said values having been derived from each of the multiple data sets collected from each observer.

(i) In one embodiment, the means and standard deviations of the distributions of the values of the internal parameters of the parallel transport components associated with each observer are used to estimate the probability that these distributions are different in a statistical sense. In the example of stimuli consisting of mixtures of red and blue colors: this test would determine to what extent two observers perceived various colors in the database as being related by certain color transformations that they agreed by convention to call "one shade redder" and "one shade bluer."

(b) The perceptions of two groups of observers can be compared by using statistical measures of the differences between the distributions of the values of the internal parameters of the parallel transport components, said values having been derived from data sets collected from each member of the two groups.

(i) In one embodiment, the means and standard deviations of the distributions of the values of the internal parameters of the parallel transport components, said distributions being associated with each of the two groups, are used to estimate the probability that these distributions are different in a statistical sense.

(c) The perceptions of one specific observer and a group of observers can be compared by using statistical measures of the differences between the distributions of the values of the internal parameters of the parallel transport components, said values having been derived from multiple data sets collected from the specific observer and from data sets collected from each member of the group of observers.

(i) In one embodiment, the means and standard deviations of the distributions of the values of the internal parameters of the parallel transport components, said distributions being associated with the specific observer and with the group of observers, are used to estimate the probability that these distributions are different in a statistical sense.

((i)) In one embodiment, this method can be used to determine if the visual perception of a specific observer is different from that of a group of observers, called "normal" observers. In the example of stimuli consisting of mixtures of red and blue colors: this method could be used to determine if a specific observer perceived color mixtures in the same way as a group of "normal" observers.

((ii)) In one embodiment, this method can be used to determine if the auditory perception of a specific observer is different from that of a group of observers, called "normal" observers.

D. Emulating the Perception of an Observer

Figure 11:
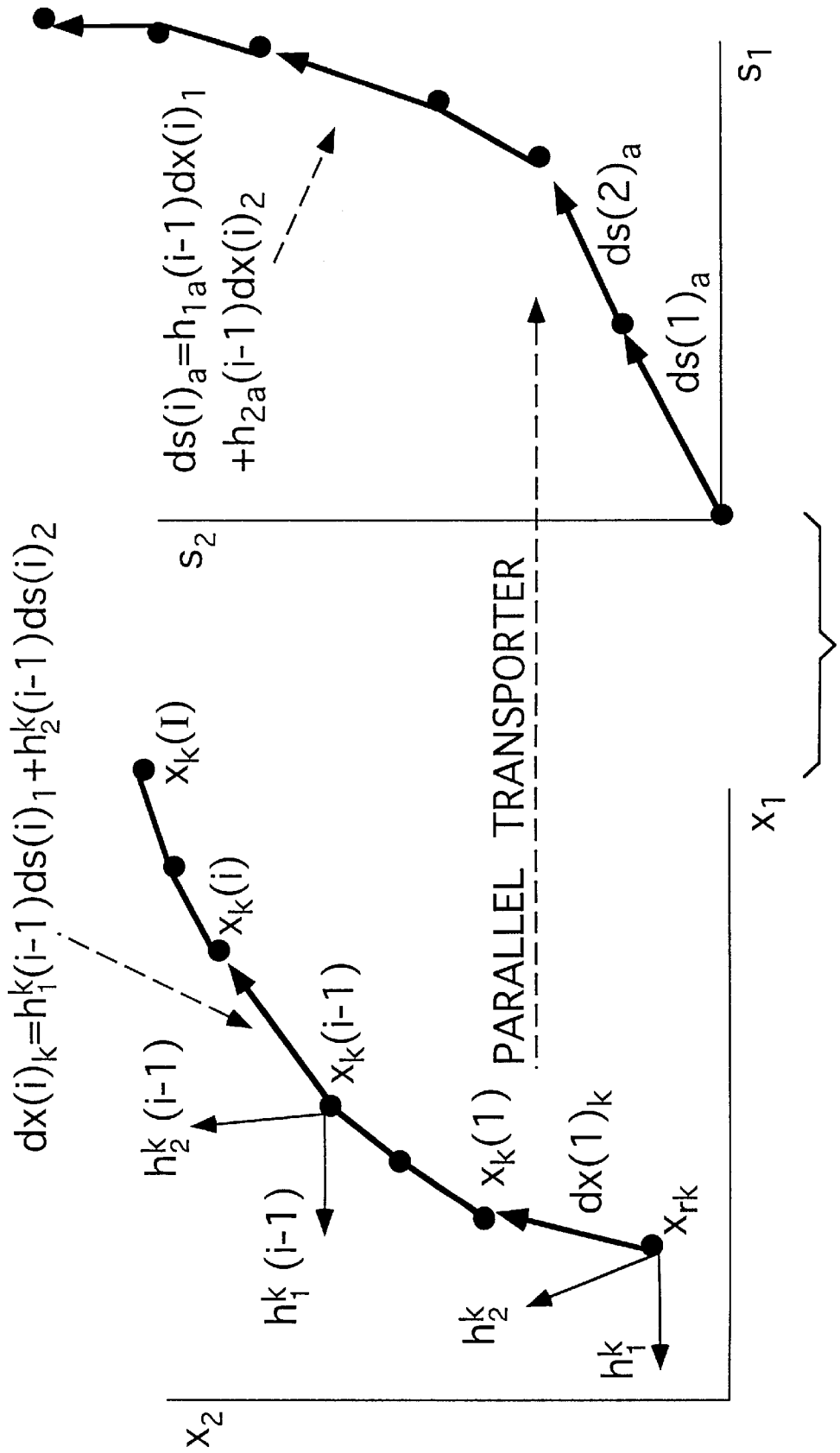
FIG. 11. The parallel transport component for an observer can be used to emulate the observer's description of a sequence of stimuli with coordinates $x_k(i)$. The stimuli are described in terms of a sequence of transformations, each of which is perceptually equivalent to a weighted combination of reference transformations of the initial stimulus in the sequence. The reference transformations of the reference stimulus are determined by the vectors $h_a^k$, and their weighting in the transformation from stimulus $i-1$ to stimulus $i$ is given by the numbers $ds(i)_a$.

The measurements described in IIIB1 are collected from the observer to be emulated and used to determine the internal parameters of the parallel transport component, according to the methods in IIIB2. The stimulus of interest is chosen from the stimulus database by the operator, using the stimulus manipulation device (FIG. 11). Alternatively, the stimulus of interest is selected from the stimulus database by the computer program, based on data recorded by the stimulus recording device. In one embodiment, the computer selects the stimulus in the stimulus database that has the most similarity to the stimulus recorded by the stimulus recording device. The coordinates of the stimulus of interest $x_k$ are stored in computer memory. A reference stimulus is chosen by the operator using the stimulus manipulation device. Alternatively, the reference stimulus is specified by the computer program. The coordinates of the reference stimulus $x_{rk}$ are stored in computer memory. The values of N linearly-independent reference vectors $h_a^k$ with labels $a=1, \ldots, N$ and vector indices $k=1, \ldots, N$ are chosen by the operator using the stimulus manipulation device to specify N reference transformations of the reference stimulus, said transformations being given by the sequence of stimuli with coordinates $x_{rk}+uh_a^k$ where u varies from 0 to 1. Alternatively, the vectors $h_a^k$ are specified by the computer program. The operator uses the stimulus manipulation device to select a sequence of stimuli $x_k(i)$ where $i=0, 1, \ldots, l$, where $x_k(0)=x_{rk}$, and where $x_k(l)=x_k$. Alternatively, this sequence of stimuli is specified in the computer program. The following method is used to generate a description of the sequence of stimuli $x_k(i)$ in terms of the application of a sequence of transformations to them. The values of $ds(i)_a$ are equal to $ds(i)_a=h(i-1)_{ka}dx(i)_k$ where $dx(i)_k=x_k(i)-x_k(i-1)$, where $h(i)_{ka}$ is obtained from $h(i)_a^k$ by solving the linear equations $$\sum_{a=1,\ldots,N} h(i)_{ka} h(i)_a^l = \delta_k^l,$$

and where $h(i)_a^k$ is obtained by using the parallel transport component to operate on the numbers $(x_k(i-1), h(i-1)_a^k, dx_k(i))$, and where $h(0)_a^k=h_a^k$. The description of the sequence of stimuli $x_k(i)$ by the observer of interest is emulated by the sequence of l statements, the $i^{th}$ said statement in the description being: "Next, the stimulus was changed by a transformation, said transformation being perceptually equivalent to the combination of reference transformations of the reference stimulus, with the $a^{th}$ said reference transformation in the combination having size $ds(i)_a$." In the example of stimuli consisting of mixtures of red and blue colors: if a color detected by the stimulus recording device matched a color in the stimulus database, the apparatus could compute how an observer would describe it as being a certain number of shades redder and/or bluer than any other color in the stimulus database.

(a) In one embodiment, the parallel transport component is given by Eqs.[9–10] omitting terms in Eq.[10] with $j>1$. The numbers $ds(i)_a$ are computed from $$s_a(i) = \sum_{k=1,\ldots,N} h_{ka}[x_k(i) - x_{rk}] - \qquad \text{Eq. (20)}$$

$$\sum_{k,l,m=1,\ldots,N} \Gamma_{lm}^k(x_r) h_{ka} \sum_{j=1,\ldots,i} [x_l(j) - x_l(i)] dx(j)_m -$$

$$\sum_{i,j,k,l,m=1,\ldots,N} [\partial_i \Gamma_{lm}^k(x_0) + \Gamma_{lm}^j(x_0)\Gamma_{ji}^k(x_0)] h_{ka} \sum_{j=1,\ldots,i} [x_l(j) - x_l(i)][x_{i'}(j) - x_{n'}] dx(j)_m$$

where $$s_a(i) = \sum_{j=1,\ldots,i} ds(j)_a,$$

where $h_{ka}$ is derived by solving the linear equations $$\sum_{a=1,\ldots,N} h_{ka} h_a^l = \delta_k^l,$$

and where $\Gamma_{lm}^k(x)$ is given by Eq.[10] omitting terms with $j>1$.

(b) In another embodiment, the parallel transport component is given by Eq.[9] and Eqs.[11–13], omitting terms in Eq.[12] with $j>2$. The numbers $ds(i)_a$ are computed from Eq.[20] where $$s_a(i) = \sum_{j=1,\ldots,N} ds(j)_a,$$

where $h_{ka}$ is derived by solving the linear equations $$\sum_{a=1,\ldots,N} h_{ka} h_a^l = \delta_k^l,$$

and where $\Gamma_{lm}^k(x)$ is given by Eqs.[11–13], omitting terms with $j>2$ in Eq.[12].

(c) In another embodiment, the parallel transporter is given by a neural network, implemented in hardware or software, with the internal parameters determined according to the methods in IIIB2 from the measurements collected from the observer as in IIIB1

E. Translation and Transduction of the Perceptions of Two Observers

Figure 12:
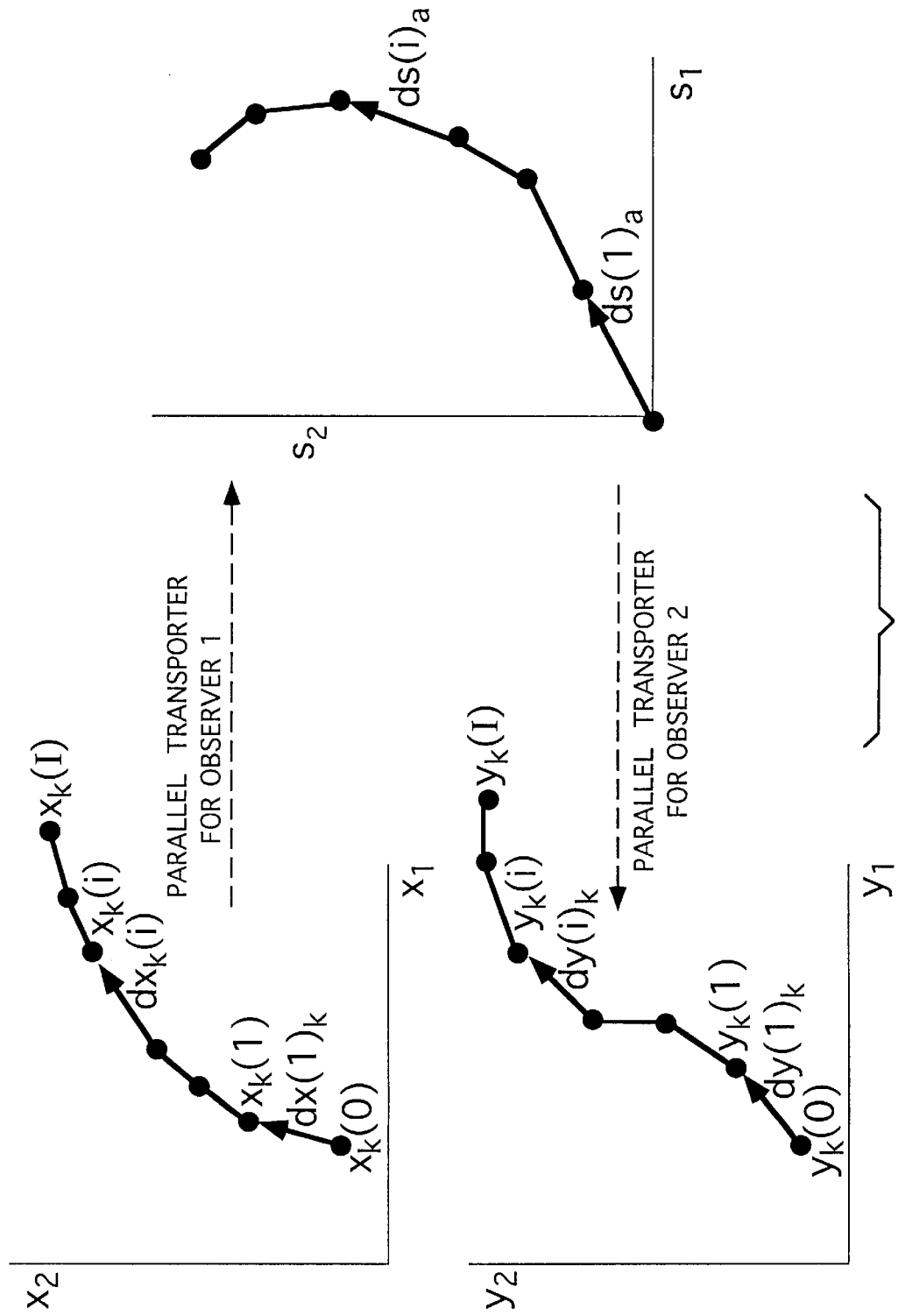
FIG. 12. The parallel transport components for two observers can be used to derive the coordinates $y_k(i)$ of a sequence of stimuli in stimulus database $S_2$ that observer 2 describes in the same way that observer 1 describes the sequence of stimuli with coordinates $x_k(i)$ in stimulus database $S_1$.

The following is the procedure for computing the coordinates of a sequence of stimuli in one stimulus database $S_2$ that is described by one observer $Ob_2$ in the same way as another sequence of stimuli in another stimulus database $S_1$ is described by another observer $Ob_1$ (FIG. 12). The internal parameters of the parallel transport components for the two observers are determined by applying the methods in IIIB2 to the measurements collected from $Ob_1$ using the stimulus database $S_1$ and to measurements collected from $Ob_2$ using stimulus database $S_2$. The coordinates $x_k(i)$ of any sequence of stimuli (labeled by $i=0, 1, \ldots, l$) in the stimulus database $S_1$ are chosen by the operator, using the stimulus manipulation device. Alternatively, these coordinates are specified by the computer program. These coordinates are stored in the memory of the computer. The methods in IIID are applied to these coordinates with $x_k(0)$ taken to be the reference stimulus, with the reference vectors being denoted by $h_a^k$, and with the internal parameters of the parallel transport component being those derived for $Ob_1$. This process determines the numbers $ds(i)_a$ that determine l statements, said statements emulating $Ob_1$'s perception of the transformations that lead from one stimulus in the sequence to the next stimulus in the sequence. The operator uses the stimulus manipulation device to choose a reference stimulus in the stimulus database $S_2$, said stimulus having coordinates $y_k(0)$. The operator also chooses N linearly independent reference vectors $g_a^k$ associated with transformations of that reference stimulus, said transformations given by the sequence of stimuli with coordinates $y_k(0)+ug_a^k$ where u varies from 0 to 1. Alternatively, the values of $y_k(0)$ and $g_a^k$ are specified by the computer program. The parallel transport component, having internal parameters set equal to those values derived for $Ob_2$, is used to generate a sequence of stimulus coordinates $y_k(i)$ of stimuli in $S_2$ by: 1) setting $y_k(1)=y_k(0)+dy(1)_k$ where $$dy(1)_k = \sum_{a=1,\ldots,N} g_a^k ds(1)_a,$$

2) setting $y_k(2)=y_k(0)+dy(1)_k+dy(2)_k$ where $dy(2)_k$ is obtained by using the parallel transporter to map the numbers $(y_k(0),$ $$\sum_{a=1,\ldots,N} g_a^k ds(2)_a,$$

$dy(1)_k)$ onto $dy(2)_k$, 3) setting $y_k(3)=y_k(0)+dy(1)_k+dy(2)_k+dy(3)_k$ where $dy(3)_k$ is obtained by first using the parallel transporter to map $(y_k(0),$ $$\sum_{a=1,\ldots,N} g_a{}^k ds(3)_a, dy(1)_k)$$

onto the numbers $dy(3,1)_k$ and then using the parallel transporter to map $(y_k(0)+dy(1)_k, dy(3,1)_k, dy(2)_k)$ onto $dy(3)_k$, 4) continuing in this way to generate coordinates of stimuli in $S_2$ from the numbers $ds(i)_a$. If the methods of IIID are applied to the sequence of stimuli in $S_2$ having coordinates $y_k(i)$, with the internal parameters of the parallel transport component equal to those determined for $Ob_{2''}$ with the reference stimulus having coordinates $y_k(0)$, and with reference vectors $g_a{}^k$, then the resulting descriptive statements are the same as those that result when the methods of IIID are applied to the sequence of stimuli in $S_1$ having coordinates $x_k(i)$, with the internal parameters of the parallel transport component equal to those determined for $Ob_1$, with the reference stimulus having coordinates $x_k(0)$, and with the reference vectors equal to $h_a{}^k$. The sequence of stimuli with coordinates $y_k(i)$ are said to represent the stimuli in $S_2$ produced by translating or transducing the stimuli in $S_1$ with coordinates $x_k(i)$, said translation or transduction being from the perceptual space of $Ob_1$ to the perceptual space of $Ob_2$. In the example of stimuli consisting of mixtures of red and blue colors perceived differently by two observers: given any sequence of colors observed by one observer, the apparatus could compute another sequence of colors that the other observer would perceive in the same way.

(a) In one embodiment, the parallel transport component for $Ob_2$ is represented by Eq.[9–10], omitting terms in Eq.[10] with j>1. The sequence of numbers $ds(i)_a$, determined from the coordinates $x_k(i)$ with the parallel transport component of $Ob_1$, is substituted into $$y_k(i) = y_k(0) + \sum_{a=1,\ldots,N} g_a{}^k s_a(i) + \quad \text{Eq. (21)}$$

$$\sum_{l,m,a,b=1,\ldots,N} \Gamma_{lm}^k(y_k(0)) g_a{}^l g_b{}^m \sum_{j=1,\ldots,i} [s_a(j) - s_a(i)] ds(j)_b +$$

$$\sum_{i',j,l,m,a,b,c+1,\ldots,N} [\partial_{i'} \Gamma_{lm}^k(y_0) - \Gamma_{jm}^k(y_0) \Gamma_{li'}^j(y_0) -$$

$$\Gamma_{lj}^k(y_0) \Gamma_{mi'}^j(y_0)] g_a{}^l g_b{}^j g_c{}^m \sum_{j=1,\ldots,i} [s_a(j) - s_a(i)] s_b(j) ds(j)_c$$

where $$s_a(i) = \sum_{j=1,\ldots,i} ds(j)_a,$$

where $\Gamma_{lm}{}^k(x)$ is given by Eq.[10] with $x_0=y_0$ and without the terms for j>1, and where all internal parameters of the parallel transport component in this equation and the value of $y_0$ are those determined for $Ob_2$. If the methods of IIID are applied to the sequence of stimuli in $S_2$ having coordinates $y_k(i)$, with the internal parameters of the parallel transport component equal to those determined for $Ob_{2''}$ with the reference stimulus having coordinates $y_k(0)$, and with reference vectors $g_a{}^k$, then the resulting descriptive statements are the same as those that result when the methods of IIID are applied to the sequence of stimuli in $S_1$ having coordinates $x_k(i)$, with the internal parameters of the parallel transport component equal to those determined for $Ob_1$, with the reference stimulus having coordinates $x_k(0)$, and with the reference vectors equal to $h_a{}^k$.

(b) In another embodiment, the parallel transport component for $Ob_2$ is represented by Eq.[9] and Eqs.[11–13], omitting terms in Eq.[12] with j>2. The sequence of numbers $ds(i)_a$, determined by applying the methods in IIID to the coordinates $x_k(i)$ with the parallel transport component of $Ob_1$, are substituted into Eq.[21] where $$s_a(i) = \sum_{j=1,\ldots,i} ds(j)_a,$$

where $\Gamma_{lm}{}^k(x)$ is given by Eqs.[11–13] without the terms for j>2 in Eq.[12], and where $y_0$ and all internal parameters of the parallel transport component in this equation are those determined for $Ob_2$. If the methods of IIID are applied to the sequence of stimuli in $S_2$ having coordinates $y_k(i)$, with the internal parameters of the parallel transport component equal to those determined for $Ob_{2''}$ with the reference stimulus having coordinates $y_k(0)$, and with reference vectors $g_a{}^k$, then the resulting descriptive statements are the same as those that result when the methods of IIID are applied to the sequence of stimuli in $S_1$ having coordinates $x_k(i)$, with the internal parameters of the parallel transport component equal to those determined for $Ob_1$, with the reference stimulus having coordinates $x_k(0)$, and with the reference vectors equal to $h_a{}^k$.

(c) In another embodiment, the parallel transport components for $Ob_1$ and $Ob_2$ are implemented in hardware or software as neural networks with internal parameters equal to the values determined by applying the methods of IIIB2 to the data collected from $Ob_1$ and $Ob_2$, respectively, said collection being done according to the methods of IIIB1.

(d) In one embodiment, the method is used to generate the coordinates of a sequence of visual stimuli in $S_2$ that one observer $Ob_2$ describes in the same way as another sequence of visual stimuli in $S_1$ is described by a another observer $Ob_1$.

(e) In one embodiment, the method is used to generate the coordinates of a sequence of auditory stimuli in $S_2$ that one observer $Ob_2$ describes in the same way as another sequence of auditory stimuli in $S_1$ is described by a another observer $Ob_1$.

(f) In one embodiment, the method is used to generate the coordinates of a sequence of auditory stimuli in $S_2$ that one observer $Ob_2$ describes in the same way as another sequence of visual stimuli in $S_1$ is described by a another observer $Ob_1$. In the example of one stimulus database consisting of mixtures of red and blue colors and a second stimulus database consisting of mixtures of two tones: given any sequence of colors described by one observer in terms of changes in shades of red and blue, the apparatus could compute a series of sounds that would be perceived by another observer as a sequence of analogous changes in the pitches of the two tones. The second observer could use the tones to "hear" what color was observed by the first observer.

(g) In one embodiment, the method is used to generate the coordinates of a sequence of visual stimuli in $S_2$ that one observer $Ob_2$ describes in the same way as another sequence of auditory stimuli in $S_1$ is described by a another observer $Ob_1$.

IV. DISCUSSION

The novel inventive method and apparatus described herein is based on the following assumption: if two stimuli differ by a small transformation, an observer can identify a small transformation of one stimulus that is perceptually equivalent to any small transformation of the other stimulus. Differential geometry provides the natural mathematical language for describing such equivalence relations between transformations. Specifically, these equivalence relations endow the stimulus manifold with structure, represented by an affine connection. The affinity provides a way of describing the essential perceptual experience of the observer without modeling the mechanism of perception. Therefore, it can be applied to a wide variety of observers (humans and machines) and to diverse types of stimuli. The affinity characterizes how an observer will describe any evolving stimulus in terms of other perceptual experiences; i.e. in terms of a reference stimulus and reference transformations (FIG. 2). The perceptual systems of two observers can be compared by comparing the values of their affinities and certain derived quantities, such as geodesics and curvature. One can also compare their coordinate-independent descriptions of the same physical phenomenon (FIG. 3a). Furthermore, the measured affinities can be used to map any stimulus perceived by one observer onto another stimulus that a second observer perceives to be the result of the same sequence of transformations, starting with the same initial stimulus state. This constitutes a kind of "translation" or "transduction" of stimuli from one perceptual space to another perceptual space (FIGS. 3a,b). This is possible even if the two manifolds describe different physical phenomena; for example, in principle, an evolving visual stimulus could be mapped onto an evolving auditory stimulus so that the latter is heard by a second observer in the same relative way as the former is seen by a first observer.

There are theoretical grounds for expecting common perceptual experiences to be described by nearly flat manifolds with nearly symmetric connections. Flat manifolds have the feature that there is one and only one transformation of each stimulus that is perceptually equivalent to each transformation of a reference stimulus in the manifold. Thus, the observer perceives "local" transformations in a consistent and reproducible way; i.e. he does not "lose his bearings". Furthermore, flat symmetric connections have the property that every sequence of transformations connecting two stimuli is associated with the same net coordinate-independent description $s_a$; i.e. the observer perceives the same net relationship between two stimuli no matter how one of them was transformed into the other one. Thus, the observer should be able to recognize a stimulus state that is revisited after being exposed to other stimuli; i.e. he does not become "lost". Mathematically, this means that the net coordinate-independent transformation is a "path independent" quantity that defines the geodesic coordinates of each stimulus. In principle, the observer could use these coordinates to keep track of his/her location relative to any previously visited stimuli. In short, the observer could use the rules of planar coordinate geometry to "navigate" through a wide range of stimuli without losing a sense of location or orientation on the stimulus manifold. This seems to match the common perceptual experience of most normal observers. It will be interesting to see if this expectation is borne out experimentally.

Curved manifolds describe a more confusing and unfamiliar perceptual experience. The transformation of one stimulus that is perceptually equivalent to a transformation of another stimulus may depend on the path traversed between the two stimuli. Thus, unless curvature is explicitly taken into account, the observer's interpretation of a transformation of a given stimulus may depend on how that stimulus state was created in the first place. Such an observer could become "disoriented" if a stimulus was revisited and the current perception of a transformation conflicted with one in memory. Furthermore, curvature and/or asymmetry of the affinity imply that different sequences of transformations between two stimuli may be associated with different values of the net coordinate-independent transformation perceived by the observer. Therefore, unless the observer explicitly accounts for this effect, the relationship perceived between the two states could depend on how one of them was transformed into the other. For example, such an observer could fail to recognize a stimulus state which was revisited. This path-dependence of the recognition process is reminiscent of some cases of abnormal perception described in the neurological literature (Sacks, Oliver. An Anthropologist on Mars. New York: Alfred A. Knopf, 1995. Sacks, Oliver. The Man Who Mistook His Wife for a Hat. New York, Harper Collins, 1985.). For instance, it bears some resemblance to the perceptual experience of persons who were blind until late in life. Some patients afflicted with agnosia have also been reported to suffer from various types of perceptual dislocation and disorientation (Farah, Martha J. Visual Agnosia. Cambridge, Mass: MIT Press, 1990). One could imagine even more confusing situations in which the manifold of internally-generated thoughts was curved. Of course, these are speculations which must be tested by detailed experimentation.

The perceptions of two observers will be identical if and only if their affinities are identical. Symmetric affinities are identical if and only if they have identical families of geodesic trajectories with identical "metrics" along them. A special type of perceptual discrepancy is worth noting: suppose the affine connections of two observers differ by terms of the type $\delta_l^k U_m + \delta_m^k U_l$, where $U_m$ is an arbitrary vector field. Then, corresponding geodesics have identical shapes but different "metrics". For example, this would happen if one listener perceived pitch intervals having equal frequency differences to be equivalent, and another listener perceived pitch increments having equal frequency ratios to be equivalent. In general, the affine connections of two observers may differ because of variations at any point in the perceptual process. There could be acquired or congenital differences in the structures of their sensory organs or brains. Variations of brain function caused by exogenous or endogenous substances could lead to different perceptual spaces. Differences in past perceptual experience or "training" could also influence the values of the affine connection. Since the methods in this article do not model the perceptual mechanisms of the observer, they cannot identify the reason why two observers do not "see" stimuli in the same way. However, these methods may make it possible to identify groups of subjects that have characteristic forms of the affine connection. This type of empirical classification could suggest models for the perceptual mechanisms of these groups. It may also be useful for neurological, psychological, and psychiatric diagnosis.

In principle, the techniques described herein could be used to build a machine which emulated the perceptual performance of a given observer. Such a device would store the equivalence relations of the observer to be emulated. This could be done by measuring the observer's affine connection and explicitly encoding it in the machine's control program or hardware.

Alternatively, the device could be based on a neural net which reproduced these equivalence relations (Rumelhart, D. E. and McClelland, J. L. Parallel Distributed Processing. Explorations in the Microstructure of Cognition. Volume 1: Foundations. Cambridge, Mass.: MIT Press, 1986. McClelland, J. L. and Rumelhart, D. E. Parallel Distributed Processing. Explorations in the Microstructure of Cognition. Volume 2: Psychological and Biological Models. Cambridge, Mass.: MIT Press, 1986. McClelland, J. L. and Rumelhart, D. E. Explorations in Parallel Distributed Processing. A Handbook of Models, Programs, and Exercises.

Cambridge, Mass.: MIT Press, 1986.). In general, these equivalence relations are encoded by the parallel transport operation in Eq. [1]. Specifically, the parallel transport operation maps a transformation ($h^k$) of a stimulus point ($x_k$) onto a perceptually equivalent transformation ($h^k+\delta h^k$) of the stimulus at a neighboring point ($x_k+dx_k$). Neural networks can be "trained" to implement such a mapping so that it is consistent with the experimental measurements of transformation pairs perceived to be equivalent by a specific observer. This could be done by adjusting the weights of a neural network so that it accurately mapped each transformation of each such pair onto the other member of that pair; i.e. so that it accurately mapped $h^k$ at $x_k$ onto $h^k+\delta h^k$ at $x_k+dx_k$ for all such pairs. Such a trained network could then be used to predict other pairs of transformations that the observer would find to be perceptually equivalent.

The affine connection is sufficient to define a "metric" along each geodesic of the stimulus manifold. This can be used to compare the magnitudes of a sequence of transformations perceived to be qualitatively the same; e.g. the magnitudes of successive transformations raising the pitch of a note by various amounts. However, only flat manifolds and a subset of curved manifolds support a Riemannian metric $g_{kl}$, which agrees with the affine metric on each geodesic. Such a complete metric makes it possible to compare the magnitudes of transformations along different geodesics; e.g. to compare the magnitudes of transformations perceived to be qualitatively different. For example, a Riemannian metric on a manifold of a tone's pitch and intensity would provide an observer with a consistent way of comparing a change in the pitch of a note with a change of its intensity. If curved perceptual spaces are an experimental reality, it will be interesting to see if they satisfy the conditions necessary for the existence of a Riemannian metric.

Finally, it is worth mentioning the possibility of perceptual spaces with unusual topologies. For instance, suppose that a measured affine connection described a closed manifold, topologically equivalent to a sphere, cylinder, or torus. Such a space might have re-entrant geodesics. This means that repeated applications of perceptually equivalent transformations would return the stimulus to its original physical state. Since the observer would perceive a nonvanishing coordinate-independent transformation, he/she might fail to recognize the original state when it was revisited. This is analogous to the "Tritone Paradox" phenomenon. Theoretically, it is possible to imagine even more exotic perceptual spaces having "worm holes", "black holes", and even more unusual topologies.

Please refer to Appendix A for a source code listing of the above-described method written in the C and Mathematica programming languages and including computer generated output data associated with the program.

V. DERIVATION OF THE EQUATIONS

The derivation of Eq.[3] is presented in this appendix. Let $x_k(t)$ be any trajectory originating at the origin of the $x_k$ coordinate system; i.e. $x_k(0)=(0,0)$. Each increment $dx_k$ along the trajectory can be decomposed into components $ds_a$ along $h_a^k(t)$, the transformations at that point that are perceptually equivalent to reference transformations $h_a^k$ at the origin (FIG. 2):

$$ds_a = h_{1a}(t)dx_1 + h_{2a}(t)dx_2 \tag{a1}$$

where $h_{ka}(t)$ is defined to be the inverse of $h_a^k(t)$ $$h_{k1}(t)h_1^l(t) + h_{k2}(t)h_2^l(t) = \delta_k^l \tag{a2}$$

When the trajectory is traversed from the origin to $x_k(t)$, the perceived sequence of transformations is $$s_a(t) = \int_0^t ds_a = \int_0^t \left[ h_{1a}(u)\frac{dx_1}{du} + h_{2a}(u)\frac{dx_2}{du} \right] du \tag{A3}$$

It follows from Eq.[A2] that $h_{ka}(t)$ transforms as a covariant vector with respect to k and that its values along the trajectory change according to the covariant version of Eq.[1]

$$\delta h_{la} = \sum_{k,m=1,2}^{a} \Gamma_{lm}^k(x) h_{ka} dx_m \tag{A4}$$

This is equivalent to the integral equation $$h_{la}(t) = h_{la}(0) + \sum_{k,m=1,2} \int_0^t \Gamma_{lm}^k(x) h_{ka}(u) \frac{dx_m}{du} du \tag{A5}$$

When Eq.[A5] is substituted into Eq.[A3], the second term of the resulting expression can be integrated by parts to give $$s_a(t) = \sum_{l=1,2} h_{la}(0) x_l(t) - \sum_{k,l,m=1,2} \int_0^t [x_l(u) - x_l(t)] \Gamma_{lm}^k(x) h_{ka}(u) \frac{dx_m}{du} du \tag{A6}$$

When Eq.[A5] is expanded as a power series in $x_k(t)$, the first two terms are $$h_{la}(t) = h_{la}(0) + \sum_{k,m=1,2} \Gamma_{lm}^k(0) h_{ka}(0) x_m(t) + \ldots \tag{A7}$$

The first three terms in the power series expansion of $s_a(t)$ can be derived by substituting Eq.[A7] into Eq.[A6], along with the first order Taylor series for the affinity in the region of the origin. The resulting expression is the same as Eq.[3], once the origin of the coordinate system is translated away from the origin of the trajectory.

Consider the special case of a trajectory $x_k(t)$ which forms a loop returning to the origin. Then, Stoke's theorem can be used to simplify the integrals in Eq.[3] in order to derive the following expression for the net perceived transformation around the circuit $$\Delta s_a = -\left( A + \sum_{l,m=1,2} \Gamma_{lm}^l \int_A x_m d^2x \right) \sum_{k=1,2} V^k h_{ka} - \sum_{k,m=1,2} \left( h_{ka} \int_A x_m d^2x \right) \left( B_{m12}^k + \frac{\Delta V^k}{\Delta x_m} \right) \tag{A8}$$

where $$\frac{\Delta V^k}{\Delta x_m} = \frac{\partial V^k}{\partial x_m} + \sum_{l=1,2} (\Gamma_{bm}^k V^l - \Gamma_{lm}^l V^k) \tag{A9}$$

is the covariant derivative of $V^k$ and all of the quantities in Eq.[8] are evaluated at the origin. If there is no net perceived transformation for every circuit-like trajectory, Eq.[A8] implies that the curvature is zero and the affinity is symmetric, as stated in Eq.[5]. If Eq.[5] is not true, Eq.[A8] shows that the net perceived transformation in the a direction may still be small if $h_{ka}$ is nearly perpendicular to $V_k$ and the first moment of the trajectory is along an eigenvector of $$B_{m12}^k + \frac{\Delta V^k}{\Delta x_m}$$

with a small eigenvalue.

Eq.[4] can be derived by using methods analogous to those presented above.

What is claimed is:

1. A method for measuring perception of an observer, the method using a stimulus output device for presenting stimuli to the observer, and a stimulus manipulation device permitting the observer to modify the presented stimuli by selecting related stimuli from a database of stimuli, the method comprising the steps of:

a) selecting a sequence of stimuli from the database of stimuli, said stimuli represented as stimulus points contained in a stimulus space;

b) determining a reference transformation of a beginning stimulus point of the sequence of stimuli, the reference transformation being presented to the observer by the stimulus output device;

c) selecting a limited portion of the sequence of stimuli, the limited portion of the sequence defined between the beginning stimulus point and an ending stimulus point, the limited portion of the sequence being presented to the observer by the stimulus output device;

d) determining an observer-defined transformation applied to the ending stimulus point of the limited portion of the sequence such that the observer perceives the observer-defined transformation applied to the ending stimulus point to be perceptually equivalent to the reference transformation applied to the beginning stimulus point;

e) selecting a new limited portion of the sequence of stimuli, the new limited portion of the sequence defined by stimulus points selected from the database, at least a portion of the new limited portion having stimulus points different from the stimulus points defining the previously selected limited portion of the sequence;

f) determining another observer-defined transformation applied to an ending stimulus point of the new limited portion of the sequence such that the observer perceives the observer-defined transformation to be perceptually equivalent to the previous observer-defined transformation; and g) performing steps (e) through (f) until a predetermined number of limited portions of the sequence of stimuli are processed such that the observer perceives each observer-defined transformation to be perceptually equivalent to previous observer-defined transformations.

2. The method according to claim 1 wherein at least one of the steps of selecting the sequence of stimuli from the database, determining a reference transformation of a beginning stimulus point, selecting a limited portion of the sequence of stimuli, and selecting a new limited portion of the sequence of stimuli, is performed by a computer.

3. The method according to claim 1 wherein at least one of the steps of selecting the sequence of stimuli from the database, determining a reference transformation of a beginning stimulus point, selecting a limited portion of the sequence of stimuli, and selecting a new limited portion of the sequence of stimuli, is performed by the observer using the stimulus manipulation device.

4. The method according to claim 1 wherein the limited portion of the sequence of stimuli is defined to be a single stimulus point such that the beginning stimulus point is the same as the ending stimulus point.

5. The method according to claim 1 wherein the step of determining the observer-defined transformation is performed by the observer using the stimulus manipulation device in response to observing the stimuli presented by the stimulus output device.

6. The method according to claim 1 wherein the step of determining the observer-defined transformation includes the step of recording each observer-defined transformation in a memory of a computer.

7. The method according to claim 1 wherein each new limited portion of the sequence of stimuli is a portion of sequential stimulus points, the new limited portion of the sequence defined to begin at a stimulus point located at the ending stimulus point of a prior portion of the sequence of stimuli.

8. The method according to claim 1 wherein the predetermined number of limited portions of the sequence of stimuli are processed until each stimulus point in the sequence of stimuli in the database of stimuli is processed.

9. The method according to claim 1 wherein the observer perceives a stimulus presented by the stimulus output device, the stimulus output device being at least one of a visual display device displaying the sequence of visual stimuli, and an audio output device producing the sequence of audio stimuli.

10. The method according to claim 9 wherein a computer stores the sequence of visual stimuli to be presented by the visual display device to the observer, the computer storing the sequence in the form of computer files, data comprising the computer files recorded from the group of devices consisting of video cameras, CCD cameras, optical photographic devices, optical microscopes, microwave detectors, x-ray radiography/tomography devices, radio frequency/MRI detecting devices, radioactivity detectors, ultrasonic detectors, and ultrasonic scanning devices.

11. The method according to claim 9 wherein a computer stores the sequence of audio stimuli to be presented by the audio output device to the observer, the computer storing the sequence in the form of computer files, data comprising the computer files recorded from microphones.

12. The method according to claim 1 wherein the step of determining the observer-defined transformation applied to at least one of the beginning stimulus point and the ending stimulus point includes the step of the observer using the stimulus manipulation device to modify the presented stimuli by selecting related stimuli from the database of stimuli, to create a transformation of the stimulus point, said transformation of the stimulus point displayed on the stimulus display device according to observer-defined preferences.

13. An apparatus for measuring perception of an observer comprising:

a) a stimulus output device for presenting stimuli to the observer;

b) a stimulus manipulation device permitting the observer to modify the presented stimuli by selecting related stimuli from a database of stimuli, said stimuli represented as stimulus points contained in a stimulus space;

c) a computer operatively coupled to the stimulus output device and operatively coupled to the stimulus manipulation device, the computer accessing the database of stimuli;

d) said stimulus manipulation device permitting observer selection of a sequence of stimuli from the database and permitting observer determination of a reference transformation of a beginning stimulus point of the sequence of stimuli, said reference transformation being presented to the observer by the stimulus output device;

e) said stimulus manipulation device permitting observer selection of a limited portion of the sequence of stimuli, the limited portion of the sequence defined between the beginning stimulus point and an ending stimulus point, the limited portion of the sequence being presented to the observer by the stimulus output device;

f) said observer determining an observer-defined transformation applied to the ending stimulus point of the limited portion of the sequence such that the observer perceives the observer-defined transformation applied to the ending stimulus point to be perceptually equivalent to the reference transformation applied to the beginning stimulus point; and g) said computer recording the sequence of stimuli and each observer-defined transformation in a memory of the computer.

14. A method for measuring perception of an observer, the method using a stimulus output device for presenting stimuli to the observer, and a stimulus manipulation device permitting the observer to modify the presented stimuli by selecting related stimuli from a database of stimuli, the method comprising the steps of:

a) selecting a plurality of stimulus points from the database of stimuli, said stimulus points contained in a stimulus space;

b) presenting a selected stimulus point to the observer by the stimulus output device, the selected stimulus point selected from the plurality of stimulus points;

c) determining a first transformation of the selected stimulus point, the first transformation being presented to the observer by the stimulus output device;

d) determining a second transformation of the selected stimulus point, the second transformation being presented to the observer by the stimulus output device;

e) determining an observer-defined transformation applied to the stimulus point resulting from application of the second transformation to the selected stimulus point, such that the observer perceives the observer-defined transformation to be perceptually equivalent to the first transformation of the selected stimulus point;

f) providing another selected stimulus point, said another selected stimulus point selected from the plurality of stimulus points; and g) performing steps (b) through (f) until a predetermined number of the plurality of stimulus points are processed.

15. The method according to claim 14 wherein at least one of the steps of selecting a plurality of stimulus points, determining a first transformation of the selected stimulus point, and determining a second transformation of the selected stimulus point, is performed by a computer.

16. The method according to claim 14 wherein at least one of the steps of selecting a plurality of stimulus points, determining a first transformation of the selected stimulus point, and determining a second transformation of the selected stimulus point, is performed by the observer using the stimulus manipulation device.

17. The method according to claim 14 wherein the selected stimulus point of the plurality of stimulus points is selected according to at least one of a random and a pseudo-random method.

18. The method according to claim 14 wherein the stimulus output device presents stimulus points and transformations of the stimulus points to the observer, the stimulus output device being at least one of a visual display device displaying a sequence of visual stimuli, and an audio output device producing a sequence of audio stimuli.

19. The method according to claim 14 wherein the step of determining the observer-defined transformation includes the step of recording each observer-defined transformation in a memory of a computer.

20. The method according to claim 14 wherein the step of determining the second transformation of the selected stimulus point is performed by the observer such that the second transformation is perceived by the observer to be perceptually different from the first transformation of the selected stimulus point.

21. The method according to claim 14 wherein the step of determining the observer-defined transformation applied to the stimulus point includes the step of the observer using the stimulus manipulation device to modify the presented stimuli by selecting related stimuli from the database of stimuli, to create a transformation of the stimulus point displayed on the stimulus display device, according to observer-defined perceptual preferences.

22. A method for measuring perception of an observer, the method using a stimulus output device for presenting stimuli to the observer, and a stimulus manipulation device permitting the observer to modify the presented stimuli by selecting related stimuli from a database of stimuli, the method comprising the steps of:

a) selecting a beginning stimulus point from the database of stimuli, the stimulus output device presenting the beginning stimulus point to the observer, the database containing a plurality of stimulus points defining a stimulus space;

b) specifying N-number of linearly independent vectors, each of the linearly independent vectors representing a transformation of the beginning stimulus point, the value of N equal to a predetermined the number of dimensions in a manifold representing the stimulus space;

c) determining M-number of transformation vectors, each transformation vector formed as a weighted combination of said N number of linearly independent vectors, each of said M-number of transformation vectors being transformations of the beginning stimulus point and having a common vertex located at the beginning stimulus point and diverging from the common vertex, each of said M-number of transformation vectors defined by a sequence of stimulus points starting at the beginning stimulus point and terminating at an ending stimulus point, each of said M-number of transformation vectors being presented to the observer by the stimulus output device; and d) determining a sequence of P-number of transformation vectors forming a connected path, each transformation vector determined by the observer such that the observer perceives each transformation vector in said sequence of P-number of transformation vectors to be perceptually equivalent to at least one of the M-number of transformation vectors having a common vertex located at the beginning stimulus point.

23. The method according to claim 22 wherein at least one of the steps of selecting the beginning stimulus point, specifying the N-number of linearly independent vectors, and determining the M-number of transformation vectors having a common vertex located at the beginning stimulus point, is performed by a computer.

24. The method according to claim 22 wherein at least one of the steps of selecting the beginning stimulus point, specifying the N-number of linearly independent vectors, determining the M-number of transformation vectors having a common vertex located at the beginning stimulus point, and determining the sequence of P-number of transformation vectors, is performed by the observer using the stimulus manipulation device.

25. The method according to claim 22 wherein the step of determining each of the P-number of observer-defined transformation vectors includes the step of recording each transformation vector in a memory of a computer.

26. The method according to claim 22 wherein at least one of the steps of determining the M-number of transformation vectors and determining the sequence of P-number of transformation vectors includes the step of the observer using the stimulus manipulation device to modify the presented stimuli by selecting related stimuli from the database of stimuli, to create a transformation of the stimulus point displayed on the stimulus display device, according to observer-defined perceptual preferences.

27. The method according to claim 22 wherein each of the M-number of transformation vectors of the beginning stimulus point are equal to each other such that each transformation vector has a same length and a same direction.

28. The method according to claim 22 wherein each of the M-number of transformation vectors of the beginning stimulus point is proportional to the other of the M-number of transformation vectors such that each transformation vector has a same direction.

29. The method according to claim 22 wherein a sequential display of stimulus points along each of the P-number of observer-defined transformation vectors is adjusted by the observer using the stimulus manipulation device so that a rate of change of the stimulus points along each transformation vector is perceived by the observer to be constant, said rate of change being recorded in a memory of a computer.

30. The method according to claim 22 wherein the sum of the M-number of transformation vectors of the beginning stimulus point is equal to zero.

31. A method for measuring and characterizing perception of a selected observer, the method using a stimulus output device for presenting stimuli and transformations of the stimuli to the observer, and a stimulus manipulation device permitting the observer to modify the presented stimuli by selecting related stimuli from a database of stimuli, to create a plurality of transformations of selected stimulus points, the stimulus points contained in the database of stimulus points defining a stimulus space, the plurality of transformations recorded in a memory of a computer, the method including the steps of:
  a) providing a parallel transporter corresponding to the selected observer, said parallel transporter receiving a beginning stimulus point, and first and second transformations of a beginning stimulus point,
  b) mapping the beginning stimulus point and the first and second transformations onto a resultant transformation of a destination stimulus point, said parallel transporter performing the mapping, said destination stimulus point formed by application of the second transformation to the beginning stimulus point, said resultant transformation perceived by the observer to be perceptually equivalent to the first transformation of the beginning stimulus point, and said parallel transporter defining an affine connection common to the first transformation, the second transformation, the resultant transformation, and the plurality of stimulus points included in the stimulus space; and
  c) storing a plurality of internal parameters of the parallel transporter in a memory of the computer, said internal parameters determining the mapping.

32. The method according to claim 31 wherein the parallel transporter is formed from a neural network such that the neural network is at least one of a back-propagation model and a self-organizing model.

33. The method according to claim 31 wherein the step of storing the internal parameters determining the mapping includes calculating an arithmetic mean and a standard deviation of a distribution of each of the internal parameters to characterize a perceptual performance of at least one of an individual observer and a group of observers, each set of internal parameters in said distribution corresponding to a mapping associated with an observer in at least one of said individual observer and a group of observers.

34. The method according to claim 31 wherein the step of storing the internal parameters is performed for a plurality of observers such that differences among the perceptions of the plurality of observers are represented by statistical measures of differences between the distributions of internal parameters corresponding to each of the observers.

35. The method according to claim 1 further including the steps of:
  a) providing a parallel transporter corresponding to a selected observer, said parallel transporter receiving the beginning stimulus point, the observer-defined transformations, and the transformations corresponding to each of the selected limited portions of the sequence of stimuli;
  b) mapping the stimulus point at the beginning of each limited portion of the sequence, the observer-defined transformation at the beginning of said limited portion, and the transformation representing said limited portion, onto a resultant transformation of the stimulus point at an end of said limited portion, the parallel transporter performing the mapping, said resultant transformation being the observer-defined transformation perceived by the observer to be perceptually equivalent to the observer-defined transformation at the beginning of said limited portion, said parallel transporter defining an affine connection common to the observer-defined transformations, the transformations representing said limited portions, and the plurality of stimulus points contained in the stimulus space; and
  c) storing a plurality of internal parameters of the parallel transporter in a memory of the computer, said internal parameters determining the mapping by the parallel transporter.

36. The method according to claim 35 wherein the parallel transporter is defined by an affine connection $\Gamma$ determined by substituting the values of the stimulus points at the beginning of said limited portions, the observer-defined transformations at the beginning and the end of said limited portions, and the transformations representing said limited portions, into the formula:

$$h^k + \delta h^k = h^k - \sum_{l,m=1,\ldots,N} \Gamma^k_{lm}(x) h^l dx_m$$

to derive constraints on said values of the internal parameters of the parallel transporter where x equals the coordinates of the stimulus point at the beginning of the limited portion, $h^k$ is the observer-defined transformation at the beginning of the limited portion, $h^k + \delta h^k$ is the observer-defined transformation at the end of the limited portion, $dx_m$ is the transformation representing the limited portion, and $\Gamma$ is affine connection at the coordinate x that depends upon the internal parameters, such that at least one of a linear regression, non-linear regression, and back-propagation technique is used to obtain the values of the internal parameters to best fit the measurements of x, $h^k$, $h^k+\delta h^k$, and $dx_m$.

37. The method according to claim 36 wherein the function $\Gamma$ is defined by first J terms in a Taylor series expansion defined by the formula:

$$\Gamma^k_{lm}(x) = \Gamma^k_{lm}(x_0) + \sum_{j=1,\ldots,J} \frac{1}{j!} \left[ \sum_{n=1,\ldots N} (x_n - x_{0n}) \frac{\partial}{\partial x_n} \right]^j \Gamma^k_{lm}(x)_{x=x_0}$$

where the values of the coefficients $\Gamma_{lm}{}^k(x_0)$ and $\partial_{n1} \ldots \partial_{nj}\Gamma_{lm}{}^k(x_0)$ are the internal parameters of the parallel transporter and $x_0$ is a selected stimulus point in the database.

38. The method according to claim 36 wherein the function $\Gamma$ has a flat-space form according to the formula:

$$\Gamma^k_{lm}(x) = - \sum_{a=1,\ldots,N} f_{la}(x) \frac{\partial}{\partial x_m} f_a^k(x)$$

where the N functions $f_a{}^k(x)$ for a=1, ..., N are given by a Taylor series expansion with J terms according to the formula:

$$f_a^k(x) = f_a^k(x_0) + \sum_{j=1,\ldots J} \frac{1}{j!} \left[ \sum_{n=1,\ldots N} (x_n - x_{0n}) \frac{\partial}{\partial x_n} \right]^j f_a^k(x)_{x=x_0}$$

where $f_{ka}(x)$ is the inverse of $f_a{}^k(x)$, determined by solving the linear equations $$\sum_{a=1,\ldots,N} f_{la}(x) f_a^k(x) = \delta_l^k,$$

where $x_{0k}$ are the coordinates of any stimulus point in the stimulus space, $f_a{}^k(x_0)$ are any N linearly independent vectors with indices k and labels a=1, ..., N, and where $\partial_{n1} \ldots \partial_{nj} f_a{}^k(x_0)$ are the internal parameters of the parallel transporter.

39. The method according to claim 35 wherein the parallel transporter is formed from a neural network such that the neural network is at least one of a back-propagation model and a self-organizing model.

40. The method according to claim 31 further including the steps of (a) selecting a connected sequence of stimulus points defining a stimulus path;

(b) selecting a limited portion of the stimulus path defined between a beginning stimulus point and an ending stimulus point (c) selecting N-number of standard linearly-independent transformations of the beginning stimulus point, the N-number of standard transformations representing a basic stimulus change for generating a description of the stimulus path;

(d) applying the parallel transporter corresponding to the observer to the beginning stimulus point, applying the parallel transporter corresponding to the observer to the transformation representing the limited portion of the stimulus path, and applying the parallel transporter corresponding to the observer to each of the N-number of standard transformations to create resultant standard transformations of the ending stimulus point;

(e) applying the parallel transporter corresponding to the observer to the ending stimulus point, applying the parallel transporter corresponding to the observer to each of said resultant standard transformations at the ending stimulus point, and applying the parallel transporter corresponding to the observer to a transformation representing another limited portion of the connected sequence of stimuli, said another limited portion beginning at the ending stimulus point of the previous limited portion, to generate resultant standard transformations of the ending stimulus point of said another limited portion;

(f) repeating step (e) until a predetermined number of stimulus points of the stimulus path are processed, to generate standard transformations at each stimulus point along the stimulus path, said resultant standard transformations being perceived by the observer to be perceptually equivalent to the N-number of standard transformations of the beginning stimulus point; and (g) expressing each transformation representing each limited portion of the stimulus path as a numerically-weighted linear combination of the standard transformations of the stimulus point at the beginning of the limited portion, said numerically-weighted linear combination of the standard transformations having a plurality of numerical weights representing the observer's description of the limited portion in terms of the application of the linear combination of the standard transformations.

41. The method according to claim 40 wherein the connected sequence of stimulus points and the N-number of standard transformations of the beginning stimulus point are selected by the computer.

42. The method according to claim 40 wherein the connected sequence of stimulus points and the N-number of standard transformations of the beginning stimulus point are selected by the operator using the stimulus manipulation device.

43. The method according to claim 40 wherein the numerical weights are the numbers defined by $ds(i)_a$ that are computed according to the formula:

$$s_a(i) = \sum_{k=1,\ldots,N} h_{ka}[x_k(i) - x_{rk}] -$$

$$\sum_{k,l,m=1,\ldots,N} \Gamma^k_{lm}(x_r) h_{ka} \sum_{j=1,\ldots,i} [x_l(j) - x_l(i)] dx(j)_m -$$

$$\sum_{i',j,k,l,m=1,\ldots,N} [\partial_i \Gamma^k_{lm}(x_0) + \Gamma^j_{lm}(x_0)\Gamma^k_{ji'}(x_0)] h_{ka} \sum_{j=1,\ldots,i} [x_l(j) -$$

$$x_l(i)][x_{i'}(j) - x_{ri'}] dx(j)_m$$

where $$s_a(i) = \sum_{j=1,\ldots,i} ds(j)_a,$$

where $x_k(i)$ are the coordinates of the stimulus points of the connected sequence of stimulus points, where $h_a{}^k$ are the N-number of standard transformations of the beginning stimulus point $x_{rk}$, where $h_{ka}$ is derived by solving the linear equations $$\sum_{a=1,\ldots,N} h_{ka} h_a^l = \delta_k^l,$$

where $dx(i)_k$ are the transformations representing said limited portions, and where $\Gamma_{lm}{}^k(x)$ is the affine connection given by the equation:

$$\Gamma^k_{lm}(x) = \Gamma^k_{lm}(x_0) +$$

$$\sum_{j=1,\ldots J} \frac{1}{j!} \left[ \sum_{n=1,\ldots,N} (x_n - x_{0n}) \frac{\partial}{\partial x_n} \right]^j \Gamma^k_{lm}(x)_{x=x_0}$$

where the values of the coefficients $\Gamma_{lm}{}^k(x_0)$ and $\partial_{n1} \ldots n_j\Gamma_{lm}{}^k(x_0)$ are the internal parameters of the parallel transporter of the observer, $x_0$ is a selected stimulus point in the database, and where terms with j>1 are set equal to zero.

44. The method according to claim 43 wherein $\Gamma_{lm}{}^k(x)$ is given by the formula $$\Gamma^k_{lm}(x) = -\sum_{a=1,\ldots,N} f_{la}(x) \frac{\partial}{\partial x_m} f_a^k(x)$$

where the N functions $f_a{}^k(x)$ for a=1, . . . , N are given by a Taylor series expansion with J terms according to the formula:

$$f_a^k(x) = f_a^k(x_0) + \sum_{j=1,\ldots J} \frac{1}{j!} \left[ \sum_{n=1,\ldots,N} (x_n - x_{0n}) \frac{\partial}{\partial x_n} \right]^j f_a^k(x)_{x=x_0}$$

where $f_{ka}(x)$ is the inverse of $f_a{}^k(x)$, determined by solving the linear equations $$\sum_{a=1,\ldots,N} f_{la}(x) f_a^k(x) = \delta_l^k,$$

where $x_{0k}$ are the coordinates of any stimulus point in the stimulus space, $f_a{}^k(x_0)$ are any N linearly independent vectors with indices k and labels a=1, . . . , N, and where $\partial_{n1} \ldots \partial_{nj} f_a{}^k(x_0)$ are the internal parameters of the parallel transporter of the observer where terms with j>2 are set equal to zero.

45. The method according to claim 40 in which the parallel transporter is given by a neural network implemented in at least one of a hardware configuration and a software configuration.

46. The method according to claim 31 further including the steps of
    (a) selecting a stimulus point in the stimulus space, selecting N-number of linearly-independent vectors representing N-number of standard transformations of the selected stimulus point, and selecting an ordered sequence of Q-number of sets of transformation vector weights, each set in the sequence having N-number of weights;
    (b) applying a transformation to the selected stimulus point, said transformation being a first linear combination of the N-number of standard transformations, said N-number of weights in the linear combination being equal to a first set of the ordered sequence of Q-number sets of weights, said transformation resulting in a first destination stimulus point;
    (c) applying the parallel transporter corresponding to the selected observer to the selected stimulus point, applying the parallel transporter corresponding to the selected observer to each of the N-number of standard transformations, and applying the parallel transporter corresponding to the selected observer to the transformation equal to said linear combination of N-number of standard transformations, to produce N-number of standard transformations at the first destination stimulus point;
    (d) applying a next transformation to said first destination stimulus point, said next transformation being the next linear combination of said N-number of standard transformations at said first destination stimulus point, the N-number of weights in said the next linear combination being equal to the next set of the ordered sequence of sets of weights, said next transformation resulting in another destination stimulus point;
    (e) applying the parallel transporter corresponding to the selected observer to said first destination stimulus point, applying the parallel transporter corresponding to the selected observer to each of said N-number of standard transformations at said first destination stimulus point, and applying the parallel transporter corresponding to the selected observer to the transformation equal to said next linear combination of N-number of standard transformations at said first destination stimulus point, to produce N-number of standard transformations at said another destination stimulus point;
    (f) repeating steps (d) and (e) using said another destination stimulus point in place of said first destination stimulus point to generate an ordered set of Q-number of transformations, each said transformation being equal to a linear combination of the N-number of standard transformations at the previously produced destination stimulus points, the linear combination having weights equal to at least one of the ordered set of Q-number of selected sets of weights, said Q-number of transformations forming a connected path in the stimulus space beginning at the selected stimulus point, the order of the Q-number of transformations being the same as the order of the Q-number of sets of weights; and
    (g) said connected path in the stimulus space being described by the selected observer in terms of the successive application of the Q-number of transformations equal to the linear combinations of the N-number of standard transformations, and the sets of weights in said linear combinations being equal to the sets of weights in the Q-number of sets of selected transformation vector weights.

47. The method according to claim 46 wherein at least one of the selected stimulus point in the stimulus space, the N-number of vectors representing the N-number of standard transformations of the selected stimulus point, and the ordered sequence of Q-number of sets of transformation vector weights, are chosen by the computer.

48. The method according to claim 46 wherein at least one of the selected stimulus point in the stimulus space, the N-number of vectors representing the N-number of standard transformations of the selected stimulus point, and the ordered sequence of the Q-number of sets of transformation vector weights, are chosen by the selected observer.

49. The method according to claim 46 wherein the sequence of destination stimulus points $y_k(i)$ is determined by substituting the numbers $ds(i)_a$, into the formula:

$$y_k(i) = y_k(0) + \sum_{a=1,\ldots,N} g_a^k s_a(i) +$$

$$\sum_{l,m,a,b=1,\ldots,N} \Gamma^k_{lm}(y_k(0)) g_a^l g_b^m \sum_{j=1,\ldots,i} [s_a(j) - s_a(i)] ds(j)_b +$$

$$\sum_{i',j,k,l,m=1,\ldots,N} [\partial_{l'}\Gamma^k_{lm}(y_0) - \Gamma^k_{jm}(y_0)\Gamma^j_{li'}(y_0) -$$

-continued
$$[\Gamma^k_{ij}(y_0)\Gamma^j_{mi'}(y_0)]\, g_a^i g_b^{i'} g_c^m \sum_{j=1,\ldots,i} [s_a(j) - s_a(i)]s_b(j)ds(j)_c$$

where $y_k(0)$ is the selected stimulus point, $g_a^k$ are vectors representing the selected N-number of standard transformations of the selected stimulus point, $$s_a(i) = \sum_{j=1,\ldots,i} ds(j)_a,$$

$ds(j)_a$ are the ordered sequence of Q-number of sets of vector transformation weights, where $\Gamma_{lm}^k(x)$ is the affine connection given by the formula:

$$\Gamma^k_{lm}(x) = \Gamma^k_{lm}(x_0) + \sum_{j=1,\ldots,J} \frac{1}{j!} \left[\sum_{n=1,\ldots,N}(x_n - x_{0n})\frac{\partial}{\partial x_n}\right]^j \Gamma^k_{lm}(x)_{x=x_0},$$

where the values of the coefficients $\Gamma_{lm}^k(x_0)$ and $\partial_{n1} \ldots \partial_{nj}\Gamma_{lm}^k(x_0)$ are the internal parameters of the parallel transporter corresponding the selected observer and $x_0=y_0$ is a selected stimulus point in the database, and where terms with j>1 are set equal to zero.

50. The method in claim 49 in which $\Gamma_{lm}^k(x)$ is the affine connection given by the formula:

$$\Gamma^k_{lm}(x) = - \sum_{a=1,\ldots,N} f_{la}(x)\frac{\partial}{\partial x_m} f_a^k(x),$$

where the N functions $f_a^k(x)$ for a=1, ..., N are given by a Taylor series expansion with J terms according to the formula:

$$f_a^k(x) = f_a^k(x_0) + \sum_{j=1,\ldots,J} \frac{1}{j!} \left[\sum_{n=1,\ldots,N}(x_n - x_{0n})\frac{\partial}{\partial x_n}\right]^j f_a^k(x)_{x=x_0},$$

where $f_{ka}(x)$ is the inverse of $f_a^k(x)$, determined by solving the linear equations $$\sum_{a=1,\ldots,N} f_{la}(x)f_a^k(x) = \delta_l^k,$$

where $x_{0k}=y_{0k}$ is a stimulus point in the stimulus space, $f_a^k(x_0)$ are any N linearly independent vectors with indices k and labels a=1, ..., N, and where $\partial_{n1} \ldots \partial_{nj}f_a^k(x_0)$ are the internal parameters of the parallel transporter corresponding the selected observer where terms with j>2 are set equal to zero.

51. The method in claim 46 wherein the parallel transporter is implemented in at least one of a hardware configuration and a software configuration, as a neural network.

52. The method in claim 46 including the steps of
(a) selecting another stimulus space having a plurality of stimulus points, the stimulus points of the another stimulus space being at least one of identical to the stimulus points of the stimulus space and different from the stimulus points of the stimulus space;
(b) designating an another observer, the another observer being one of at least the selected observer and a new observer;
(c) deriving the ordered set of Q-number of sets of transformation vector weights from a selected sequence of stimulus points in said another stimulus space by performing the steps of:
(c1) selecting a connected sequence of stimulus points defining a stimulus path in the another stimulus space;
(c2) selecting a limited portion of the stimulus path defined between a beginning stimulus point and an ending stimulus point;
(c3) selecting N-number of standard linearly-independent transformations of the beginning stimulus point, the N-number of standard transformations representing basic stimulus changes for generating a description of the stimulus path;
(c4) applying the parallel transporter corresponding to the another observer to the beginning stimulus point, applying the parallel transporter corresponding to the another observer to the transformation representing the limited portion of the stimulus path, and applying the parallel transporter corresponding to the another observer to each of the N-number of standard transformations to create resultant standard transformations of the ending stimulus point;
(c5) applying the parallel transporter corresponding to the another observer to the ending stimulus point, applying the parallel transporter corresponding to the another observer to each of said resultant standard transformations at the ending stimulus point, and applying the parallel transporter corresponding to the another observer to a transformation representing another limited portion of the connected sequence of stimuli, said another limited portion beginning at the ending stimulus point of the previous limited portion, to generate resultant standard transformations of the ending stimulus point of said another limited portion;
(c6) repeating step (c5) until a predetermined number of stimulus points of the stimulus path are processed, to generate standard transformations at each stimulus point along the stimulus path, said resultant standard transformations being perceived by the another observer to be perceptually equivalent to the N-number of standard transformations of the beginning stimulus point;
(c7) expressing each transformation representing each limited portion of the stimulus path as a numerically-weighted linear combination of the standard transformations of the stimulus point at the beginning stimulus point of the limited portion, said numerically-weighted linear combinations of the standard transformations having a plurality of numerical weights representing the another observer's description of the connected sequence of stimuli in terms of the successive application of the standard transformations and
(d) said ordered sequence of the Q-number sets of transformation vector weights generating a sequence of stimulus points in the stimulus space such that the selected observer of the generated sequence of stimulus points perceives the generated stimulus points in the same way as the another observer of the selected sequence of stimulus points in the another stimulus space perceives the selected stimulus points in the another stimulus space.

53. The method according to claim 52 wherein the plurality of stimulus points in the another stimulus space is at least one of visual and audio stimulus points, and the plurality of stimulus points in the stimulus space is at least one of visual and audio stimulus points, said stimulus points generated in the stimulus space so that the selected observer describes the at least one of the generated visual and audio stimulus points in the same way as the another observer describes the at least one of the visual and audio stimulus points in the another stimulus space.

* * * * *

UNITED STATES PATENT AND TRADEMARK OFFICE
CERTIFICATE OF CORRECTION

PATENT NO.    : 5,860,936
DATED         : January 19, 1999
INVENTOR(S)   : Levin, David N.

It is certified that error appears in the above-identified patent and that said Letters Patent is hereby corrected as shown below:

Column 1,
Line 28, insert -- ' -- before "third".
Line 32, insert -- " -- after "yesterday".

Column 7,
Line 51, delete "," after "$s_a(t)$".
Line 54, "$\Gamma_1^k$" should be -- $\Gamma_{lm}^k$ --.

Line 60, insert -- " -- after "Equations,".

Column 8,
Lines 1 to 14, $$s_a(t) = \sum_{k=1,2} h_{ka}[x_k(t) - x_k(0)] -$$  Eq. (3)

$$\sum_{k,l,m=1,2} \Gamma_{lm}^k h_{ka} \int_0^t [x_l(u) - x_l(t)]\frac{dx_m}{du} du -$$

$$\sum_{i,j,k,l,m=1,2} \left[\frac{\partial \Gamma_{lm}^k}{\partial x_i} + \Gamma_{lm}^j \Gamma_{ji}^k\right] h_{ka} \int_0^t [x_l(u) -$$

$$x_l(t)][x_i(u) - x_i(0)]\frac{dx_m}{du} du$$

should be $$s_a(t) = \sum_{k=1,2} h_{ka}[x_k(t) - x_k(0)] - \sum_{k,l,m=1,2} \Gamma_{lm}^k h_{ka} \int_0^t [x_l(u) - x_l(t)]\frac{dx_m}{du} du \quad \text{Eq. (3)}$$

$$- \sum_{i,k,l,m=1,2} \left[\frac{\partial \Gamma_{lm}^k}{\partial x_i} + \sum_{j=1,2} \Gamma_{lm}^j \Gamma_{ji}^k\right] h_{ka} \int_0^t [x_l(u) - x_l(t)][x_i(u) - x_i(0)]\frac{dx_m}{du} du \quad --.$$

Lines 30-41, $$x_k(t) = x_k(0) + \sum_{a=1,2} h_{ka} s_a(t) +$$  Eq. (4)

$$\sum_{l,m,a,b=1,2} \Gamma_{lm}^k h_a^l h_b^m \int_0^t [s_a(u) - s_a(t)]\frac{ds_b}{du} du +$$

$$\sum_{i,j,l,m,a,b,c=1,2} \left[\frac{\partial \Gamma_{lm}^k}{\partial x_i} - \Gamma_{lm}^k \Gamma_{ij}^l - \Gamma_{il}^k \Gamma_{jm}^l\right] h_a^i h_b^l h_c^m \int_0^t [s_a(u) -$$

$$s_a(t)] s_b(u) \frac{ds_c}{du} du$$

UNITED STATES PATENT AND TRADEMARK OFFICE
CERTIFICATE OF CORRECTION

PATENT NO. : 5,860,936  
DATED : January 19, 1999  
INVENTOR(S) : Levin, David N.

Page 2 of 7

It is certified that error appears in the above-identified patent and that said Letters Patent is hereby corrected as shown below:

Lines 30-41, cont'd., should be $$-- x_k(t) = x_k(0) + \sum_{a=1,2} h_a^k s_a(t) + \sum_{l,m,a,b=1,2} \Gamma_{lm}^k h_a^l h_b^m \int_0^t [s_a(u) - s_a(t)] \frac{ds_b}{du} du \quad \text{Eq. (4)}$$

$$+ \sum_{i,l,m,a,b,c=1,2} \left[ \frac{\partial \Gamma_{lm}^k}{\partial x_i} - \sum_{j=1,2} \Gamma_{jm}^k \Gamma_{li}^j - \sum_{j=1,2} \Gamma_{lj}^k \Gamma_{mi}^j \right] h_a^l h_b^i h_c^m \int_0^t [s_a(u) - s_a(t)] s_b(u) \frac{ds_c}{du} du --.$$

Column 9,  
Line 37, insert -- ( -- after "closed".

Column 11,  
Line 21, "$h^k(1) \neq h^k(1)$" should read -- $h^k(1) \neq h^k(1)$ --.

Column 13,  
Line 12,  
"$h^k + \partial h^k = h^k - \sum_{l,m=1...N} \Gamma_{lm}^k(x) h^l dx_m$" should read -- $h^k + \delta h^k = h^k - \sum_{l,m=1...N} \Gamma_{lm}^k(x) h^l dx_m$ --.

Column 13,  
Line 23, "$\Gamma_{lm}^k(x_0)$ and $\partial_{n1}...\partial_{nj} \Gamma_{lm}^k x_0)$" should read -- $\Gamma_{lm}^k(x_0)$ and $\partial_{n1}...\partial_{nj} \Gamma_{lm}^k(x_0)$ --.

Column 14,  
Line 4, "1" should be -- I --.  
Line 38, "$x_k(1)$" should be -- $x_k(I)$ --.  
Line 54, insert -- $x_k + uh^k$ -- after "coordinates".

UNITED STATES PATENT AND TRADEMARK OFFICE
CERTIFICATE OF CORRECTION

PATENT NO. : 5,860,936
DATED : January 19, 1999
INVENTOR(S) : Levin, David N.

It is certified that error appears in the above-identified patent and that said Letters Patent is hereby corrected as shown below:

Column 17,
Lines 51 to 65,
$$x_k(i) = x_k + \sum_{a=1,\ldots,N} h_a^k s_a(i) + \quad \text{Eq. (14)}$$
$$\sum_{l,m,a,b=1,\ldots,N} \Gamma_{lm}^k(x) h_a^l h_b^m \sum_{j=1,\ldots,i} [s_a(j) - s_a(i)] ds(j)_b +$$
$$\sum_{f,j,l,m,a,b,c=1,\ldots,N} [\partial_f \Gamma_{lm}^k(x_0) - \Gamma_{jm}^k(x_0)\Gamma_{lf}^j(x_0) -$$
$$\Gamma_{lj}^k(x_0)\Gamma_{mf}^j(x_0)] h_a^l h_b^f h_c^m \sum_{j=1,\ldots,i} [s_a(j) - s_a(i)] s_b(j) ds(j)_c$$

should be $$-- x_k(i) = x_k + \sum_{a=1,\ldots,N} h_a^k s_a(i) + \sum_{l,m,a,b=1,\ldots,N} \Gamma_{lm}^k(x) h_a^l h_b^m \sum_{j=1,\ldots,i} [s_a(j) - s_a(i)] ds(j)_b \quad \text{Eq. (14)}$$
$$+ \sum_{f,l,m,a,b,c=1,\ldots,N} \left[ \partial_f \Gamma_{lm}^k(x_0) - \sum_{j=1,\ldots,N} \Gamma_{jm}^k(x_0)\Gamma_{lf}^j(x_0) - \sum_{j=1,\ldots,N} \Gamma_{lj}^k(x_0)\Gamma_{mf}^j(x_0) \right]$$
$$h_a^l h_b^f h_c^m \sum_{j=1,\ldots,i} [s_a(j) - s_a(i)] s_b(j) ds(j)_c --.$$

Column 19,
Line 32, delete "according" before "in".

Column 21,
Line 11, "1,…,1," should be -- 1,…,I, --.
Line 11, "$x_k(1) = x_k$" should read -- $x_k(I) = x_k$ --.

Line 15, "$ds(i)_a = h(i-1)_{ka} dx(i)_k$" should read $$-- ds(i)_a = \sum_{k=1,\ldots,N} h(i-1)_{ka} dx(i)_k --.$$

Line 27, "1" should be -- I --.
Lines 42-50,
$$s_a(i) = \sum_{k=1,\ldots,N} h_{ka}[x_k(i) - x_{rk}] - \quad \text{Eq. (20)}$$
$$\sum_{k,l,m=1,\ldots,N} \Gamma_{lm}^k(x_r) h_{ka} \sum_{j=1,\ldots,i} [x(j) - x(i)] dx(j)_m -$$
$$\sum_{i,j,k,l,m=1,\ldots,N} [\partial_i \Gamma_{lm}^k(x_0) + \Gamma_{lm}^k(x_0)\Gamma_{ji}^k(x_0)] h_{ka} \sum_{j=1,\ldots,i} [x(j) -$$
$$x_r(i)][x_l(j) - x_{rl}] dx(j)_m$$

UNITED STATES PATENT AND TRADEMARK OFFICE
CERTIFICATE OF CORRECTION

PATENT NO. : 5,860,936
DATED : January 19, 1999
INVENTOR(S) : Levin, David N.

It is certified that error appears in the above-identified patent and that said Letters Patent is hereby corrected as shown below:

Column 21, lines 42-50, cont'd.,
should be $$\text{Eq. (20)}$$

$$--s_a(i) = \sum_{k=1,\ldots,N} h_{ka}[x_k(i) - x_{rk}] - \sum_{k,l,m=1,\ldots,N} \Gamma^k_{lm}(x_r) h_{ka} \sum_{j=1,\ldots,i}[x_l(j) - x_l(i)]dx(j)_m$$

$$- \sum_{f,k,l,m=1,\ldots,N} \left[ \partial_f \Gamma^k_{lm}(x_0) + \sum_{j=1,\ldots,N} \Gamma^j_{lm}(x_0)\Gamma^k_{jf}(x_0) \right]$$

$$h_{ka} \sum_{j=1,\ldots,i}[x_l(j) - x_l(i)][x_f(j) - x_{rf}]dx(j)_m --.$$

Column 22,
Line 2, "$s_a(i) = \sum_{j=1,\ldots,i'} ds(j)_a$" should read $--s_a(1) = \sum_{j=1,\ldots,i} ds(j)_a --$.

Line 29, "i=0, 1, ..., 1" should be --i=0, 1, ..., I--.

Line 38, "1" should be -- I --.

Column 23,
Lines 11 and 57, "$Ob_2$," should read $--Ob_2,--$.

Lines 36-45, "
$y_k(i) = y_k(0) + \sum_{a=1,\ldots,N} g_a^k s_a(i) +$ $\sum_{l,m,a,b=1,\ldots,N} \Gamma^k_{lm}(y_k(0))g_a^l g_b^m \sum_{j=1,\ldots,i}[s_a(j) - s_a(i)]ds(j)_b +$ Eq. (21)

$\sum_{f,j,l,m,a,b,c+1,\ldots,N}[\partial_f \Gamma^k_{lm}(y_0) - \Gamma^k_{jm}(y_0)\Gamma^j_{lr}(y_0) -$ $\Gamma^k_{lj}(y_0)\Gamma^j_{mr}(y_0)] g_a^l g_b^j g_c^m \sum_{j=1,\ldots,i}[s_a(j) - s_a(i)]s_b(j)ds(j)_c$ "

should read $$--y_k(i) = y_k(0) + \sum_{a=1,\ldots,N} g_a^k s_a(i) + \sum_{l,m,a,b=1,\ldots,N} \Gamma^k_{bm}(y(0))g_a^l g_b^m \sum_{j=1,\ldots,i}[s_a(j) - s_a(i)]ds(j)_b$$

$$+ \sum_{f,l,m,a,b,c=1,\ldots,N} \left[ \partial_f \Gamma^k_{lm}(y_0) - \sum_{j=1,\ldots,N} \Gamma^k_{jm}(y_0)\Gamma^j_{lf}(y_0) - \sum_{j=1,\ldots,N} \Gamma^k_{lj}(y_0)\Gamma^j_{mf}(y_0) \right]$$

$$g_a^l g_b^f g_c^m \sum_{j=1,\ldots,i}[s_a(j) - s_a(i)]s_b(j)ds(j)_c --.$$

UNITED STATES PATENT AND TRADEMARK OFFICE
CERTIFICATE OF CORRECTION

PATENT NO. : 5,860,936
DATED : January 19, 1999
INVENTOR(S) : Levin, David N.

It is certified that error appears in the above-identified patent and that said Letters Patent is hereby corrected as shown below:

Column 24,
Line 15, "$Ob_{2,,}$" should read -- $Ob_2$,--.

Column 26,
Line 41, change "article" to -- invention --.

Column 27,
Line 59, ",the" should read -- , the --.
Line 62, "(a1)" should read -- (A1) --.
Line 65, "(a2)" should read -- (A2) --.

Column 28,
Line 3,

"$s_a(t) = \int_0^t ds_a = \int_0^t \quad \left[ h_{1a}(u)\frac{dx_1}{du} + h_{2a}(u)\frac{dx_2}{du} \right] du$" should read -- $s_a(t) = \int_0^t ds_a = \int_0^t \left[ h_{1a}(u)\frac{dx_1}{du} + h_{2a}(u)\frac{dx_2}{du} \right] du$ --.

Line 11, "$\delta h_{1a} = \sum_{k,m=1,2}^u \Gamma_{lm}^k(x) h_{ka} dx_m$" should read -- $\delta h_{1a} = \sum_{k,m=1,2} \Gamma_{lm}^k(x) h_{ka} dx_m$ --.

Column 35,
Line 40, "$\partial_{n1} \cdots \partial_{nj} \int_a^k (x_0)$" should read -- $\partial_{n1} \ldots \partial_{nj} \int_a^k (x_0)$ --.

Column 36,
Lines 42-49,

"$s_a(i) = \sum_{k=1,\ldots,N} h_{ka}[x_k(i) - x_{rk}] -$ $\sum_{k,l,m=1,\ldots,N} \Gamma_{lm}^k(x_r) h_{ka} \sum_{j=1,\ldots,i} [x(j) - x_r(j)] dx(j)_m -$ $\sum_{l',j,k,l,m=1,\ldots,N} [\partial_{l'} \Gamma_{lm}^k(x_0) + \Gamma_{l'm}^j(x_0) \Gamma_{jl}^k(x_0)] h_{ka} \sum_{j=1,\ldots,i} [x(j) -$ $x_r(i)][x_{l'}(j) - x_{rl'}] dx(j)_m$"

UNITED STATES PATENT AND TRADEMARK OFFICE
CERTIFICATE OF CORRECTION

PATENT NO. : 5,860,936  
DATED : January 19, 1999  
INVENTOR(S) : Levin, David N.

Page 6 of 7

It is certified that error appears in the above-identified patent and that said Letters Patent is hereby corrected as shown below:

Column 36, lines 42-49, cont'd.,
should read $$-- s_a(i) = \sum_{k=1,\ldots,N} h_{ka}[x_k(i) - x_{rk}] - \sum_{k,l,m=1,\ldots,N} \Gamma^k_{lm}(x_r) h_{ka} \sum_{j=1,\ldots,i} [x_l(j) - x_l(i)]dx(j)_m$$

$$- \sum_{f,k,l,m=1,\ldots,N} \left[ \partial_f \Gamma^k_{lm}(x_0) + \sum_{j=1,\ldots,N} \Gamma^j_{lm}(x_0) \Gamma^k_{jf}(x_0) \right]$$

$$h_{ka} \sum_{j=1,\ldots,i} [x_l(j) - x_l(i)][x_f(j) - x_{rf}]dx(j)_m \;--.$$

Column 37,
Line 9,
"$n_j \Gamma_{lm}^k(x_0)$" should read -- $\partial_{nj} \Gamma_{lm}^k(x_0)$ --

Column 38, line 60, to Column 39, line 4, $$" y_k(i) = y_k(0) + \sum_{a=1,\ldots,N} g_a^k s_a(i) +$$

$$\sum_{l,m,a,b=1,\ldots,N} \Gamma^k_{lm}(y_k(0)) g_a^l g_b^m \sum_{j=1,\ldots,i} [s_a(j) - s_a(i)]ds(j)_b +$$

$$\sum_{f,j,k,l,m=1,\ldots,N} [\partial_f \Gamma^k_{lm}(y_0) - \Gamma^k_{jm}(y_0) \Gamma^j_{lf}(y_0) -$$

$$\Gamma^k_{lj}(y_0) \Gamma^j_{mf}(y_0)] g_a^l g_b^f g_c^m \sum_{j=1,\ldots,i} [s_a(j) - s_a(i)]s_b(j)ds(j)_c \;"$$

should read $$-- y_k(i) = y_k(0) + \sum_{a=1,\ldots,N} g_a^k s_a(i) + \sum_{l,m,a,b=1,\ldots,N} \Gamma^k_{lm}(y(0)) g_a^l g_b^m \sum_{j=1,\ldots,i} [s_a(j) - s_a(i)]ds(j)_b$$

$$+ \sum_{f,l,m,a,b,c=1,\ldots,N} \left[ \partial_f \Gamma^k_{lm}(y_0) - \sum_{j=1,\ldots,N} \Gamma^k_{jm}(y_0) \Gamma^j_{lf}(y_0) - \sum_{j=1,\ldots,N} \Gamma^k_{lj}(y_0) \Gamma^j_{mf}(y_0) \right]$$

$$g_a^l g_b^f g_c^m \sum_{j=1,\ldots,i} [s_a(j) - s_a(i)]s_b(j)ds(j)_c \;--.$$

UNITED STATES PATENT AND TRADEMARK OFFICE
CERTIFICATE OF CORRECTION

PATENT NO. : 5,860,936
DATED : January 19, 1999
INVENTOR(S) : Levin, David N.

It is certified that error appears in the above-identified patent and that said Letters Patent is hereby corrected as shown below:

Column 39,
Line 24, insert -- to -- after "corresponding".
Line 52, insert -- to -- before "the selected".

Signed and Sealed this

Thirtieth Day of November, 2004

JON W. DUDAS
*Director of the United States Patent and Trademark Office*